US008465437B2

(12) United States Patent
Avila

(10) Patent No.: US 8,465,437 B2
(45) Date of Patent: Jun. 18, 2013

(54) METHOD AND SYSTEM FOR MEASURING LUNG TISSUE DAMAGE AND DISEASE RISK

(75) Inventor: Ricardo Avila, Clifton Park, NY (US)

(73) Assignee: Kitware, Inc., Clifton Park, NY (US)

( * ) Notice: Subject to any disclaimer, the term of this patent is extended or adjusted under 35 U.S.C. 154(b) by 676 days.

(21) Appl. No.: 12/620,577

(22) Filed: Nov. 17, 2009

(65) Prior Publication Data

US 2010/0063410 A1 Mar. 11, 2010

Related U.S. Application Data

(63) Continuation-in-part of application No. PCT/US2009/034021, filed on Feb. 13, 2009.

(60) Provisional application No. 61/099,564, filed on Sep. 23, 2008, provisional application No. 61/047,841, filed on Apr. 25, 2008, provisional application No. 61/044,411, filed on Apr. 11, 2008, provisional application No. 61/028,504, filed on Feb. 13, 2008.

(51) Int. Cl.
| *A61B 5/08* | (2006.01) |
| *G01N 23/04* | (2006.01) |
| *H05G 1/60* | (2006.01) |
| *G06K 9/00* | (2006.01) |

(52) U.S. Cl.
USPC ............... 600/529; 378/4; 378/62; 378/132; 600/532

(58) Field of Classification Search
None
See application file for complete search history.

(56) References Cited

U.S. PATENT DOCUMENTS

| 7,058,155 | B2 * | 6/2006 | Piacsek et al. ............... 378/4 |
| 2003/0018245 | A1 | 1/2003 | Kaufman et al. |
| 2004/0133100 | A1 | 7/2004 | Naghavi et al. |
| 2004/0184647 | A1 * | 9/2004 | Reeves et al. ............ 382/131 |
| 2005/0076909 | A1 * | 4/2005 | Stahmann et al. ....... 128/204.23 |
| 2005/0105788 | A1 | 5/2005 | Turek et al. |
| 2005/0213707 | A1 * | 9/2005 | Kaito .................... 378/98.12 |
| 2007/0003124 | A1 * | 1/2007 | Wood et al. .............. 382/131 |
| 2007/0019849 | A1 * | 1/2007 | Kaufman et al. .......... 382/128 |
| 2007/0071301 | A1 * | 3/2007 | Kiraly et al. ............. 382/131 |
| 2007/0167697 | A1 | 7/2007 | Avila et al. |

* cited by examiner

*Primary Examiner* — Michael Kahelin
*Assistant Examiner* — Michael J Burrage
(74) *Attorney, Agent, or Firm* — Todd L. Juneau

(57) ABSTRACT

This invention relates to a method, system, and devices relating to quantitatively measuring regional lung tissue damage by combining the CT scan measurements of the mineral density deviations and/or mineral composition deviations in airway tissue, with the measurements of airflow lung function measurements.

21 Claims, 25 Drawing Sheets

| Age | Gen | PY | Patient Code | Number | Scanner Correction | Main Bif | Comp Damage | R1 | Comp Damage | R2 | Comp Damage |
|---|---|---|---|---|---|---|---|---|---|---|---|
| 62 | | 52 | | | | | | | | | |
| 49 | F | 26.35 | 876 | 1 | 1.07 | 452 | 151 | 2.48 | 494 | 105 | 2.59 | 319 | 123 | 2.29 |
| 51 | F | 28 | 210 | 2 | 1.03 | 484 | 157 | 2.51 | 1275 | 89 | 3.07 | 1265 | 135 | 3.05 |
| 51 | F | 28 | 862 | 3 | 0.97 | 710 | 249 | 2.66 | 586 | 228 | 2.55 | 1638 | 124 | 3.18 |
| 55 | F | 26 | 141 | 4 | 1.00 | 383 | 174 | 2.32 | 460 | 190 | 2.43 | 471 | 274 | 2.29 |
| 52 | F | 2.5 | 1124 | 5 | 1.07 | 1631 | 394 | 3.09 | 1206 | 386 | 2.91 | 1157 | 496 | 2.82 |
| 53 | F | 72 | 554 | 6 | 1.03 | 435 | 194 | 2.38 | 623 | 181 | 2.65 | 494 | 234 | 2.41 |
| 54 | F | 75 | 1403 | 7 | 1.00 | 576 | 205 | 2.57 | 472 | 212 | 2.41 | 469 | 200 | 2.43 |
| 59 | F | 20 | 581 | 8 | 1.00 | 486 | 189 | 2.47 | 367 | 149 | 2.34 | 561 | 145 | 2.62 |
| 60 | F | 19.5 | 1082 | 9 | 1.00 | 292 | 291 | 0.00 | 706 | 67 | 2.81 | 1204 | 134 | 3.03 |
| 62 | F | 80 | 530 | | | | | | | | | |
| 62 | F | 80 | 632 | 10 | 1.00 | 499 | 254 | 2.39 | 542 | 224 | 2.50 | 1394 | 156 | 3.09 |
| 64 | F | 67.5 | 1406 | | | | | | | | | |
| 66 | F | 100 | 1680 | | | | | | | | | |
| 76 | F | 60 | 548 | 11 | 1.03 | 1082 | 500 | 2.76 | 750 | 439 | 2.49 | 1164 | 411 | 2.88 |
| 76 | F | 20 | 812 | 12 | 1.03 | 382 | 107 | 2.44 | 419 | 82 | 2.53 | 678 | 150 | 2.72 |
| 76 | F | 30 | 1431 | 13 | 1.00 | 1224 | 1203 | 1.31 | 1903 | 704 | 3.08 | 2075 | 251 | 3.26 |
| 88 | F | 142 | 159 | 14 | 1.07 | | | | 1198 | 416 | 2.89 | | | |

Fig. 4A

| L1 | Comp Damage | L2 | Comp Damage | FEV1/FVC | Lung Fun Correction | All PY | Lung Cancer Risk Index | Scanner Adj LDI Non Cancers | LDI Average | STDV | Airway |
|---|---|---|---|---|---|---|---|---|---|---|---|
|  |  |  |  | 73 | 0.16 |  |  |  |  |  |  |
|  |  |  |  |  | 65 |  |  |  |  |  |  |
| 363 | 2.40 | 316 | 2.21 | 78 | 0.90 | 2.77 | 2.30 | 2.56 | 2.39 | 0.15 | 128 |
| 1016 | 2.90 | 1183 | 2.99 | 74 | 0.93 |  | 2.77 | 2.98 | 2.91 | 0.23 | 162 |
| 684 | 2.68 | 587 | 2.66 | 71 | 0.95 |  | 2.53 | 2.66 | 2.75 | 0.25 | 188 |
| 590 | 2.67 | 557 | 2.60 | 80 | 0.88 |  | 2.17 | 2.46 | 2.46 | 0.17 | 183 |
| 1047 | 2.83 | 1110 | 2.77 | 84 | 0.85 |  | 2.70 | 2.96 | 2.88 | 0.13 | 435 |
| 629 | 2.70 | 620 | 2.64 | 76 | 0.91 |  | 2.49 | 2.56 | 2.56 | 0.15 | 185 |
|  |  |  |  | 68 | 0.98 |  |  |  |  |  |  |
| 652 | 2.66 | 519 | 2.56 | 59 | 1.05 | 2.65 | 2.65 | 2.53 | 2.53 | 0.10 | 193 |
| 560 | 2.54 | 548 | 2.56 | 81 | 0.87 |  | 2.19 | 2.51 | 2.51 | 0.11 | 175 |
| 551 | 2.55 | 552 | 2.58 | 74 | 0.93 |  | 2.04 | 2.19 | 2.19 | 1.24 | 171 |
|  |  |  |  | 74 | 0.93 |  |  |  |  |  |  |
| 1557 | 3.10 | 675 | 2.73 | 75 | 0.92 |  | 2.54 | 2.76 | 2.76 | 0.33 | 215 |
|  |  |  |  |  | 1.52 |  |  |  |  |  |  |
| 1172 | 2.85 | 733 | 2.61 | 57 | 1.06 |  | 2.97 | 2.79 | 2.72 | 0.16 | 428 |
| 722 | 2.67 | 1039 | 2.94 | 89 | 0.81 |  | 2.21 | 2.73 | 2.66 | 0.19 | 150 |
| 1741 | 3.11 | 1139 | 2.72 | 81 | 0.87 | 3.62 | 2.35 | 2.70 | 2.70 | 0.80 | 646 |
| 1445 | 3.01 | 614 |  | 47 | 1.14 |  | 3.62 | 3.16 | 2.95 | 0.09 | 414 |
|  |  |  |  |  | 0.16 |  |  |  |  |  |  |
|  |  |  |  |  | 60.00 |  |  |  |  |  |  |

Fig. 4B

| | | | | | | | | | | | | |
|---|---|---|---|---|---|---|---|---|---|---|---|---|
| 47 | M | 42 | 1118 | | 1 | 1.00 | 810 | 224 | 2.77 | 695.5 | 203 | 2.69 | 772.5 | 99 | 2.83 |
| 48 | M | 40 | 1172a | | | | | | | | | | | | |
| 48 | M | 40 | 1172b | Large | 2 | 1.07 | 437.5 | 101 | 2.53 | 362 | 121 | 2.38 | 440.5 | 142 | 2.47 |
| 48 | M | 39 | 1369 | | 3 | 1.00 | 573 | 181 | 2.59 | 614.5 | 172 | 2.65 | 841 | 238 | 2.78 |
| 49 | M | 40 | 1078 | | 4 | 1.07 | 813 | 279 | 2.73 | 480.5 | 156 | 2.51 | 415.5 | 36 | 2.58 |
| 51 | M | 37.5 | 787 | | 5 | 0.97 | 850.5 | 135 | 2.85 | 1061.5 | 182 | 2.94 | 794.5 | 68 | 2.86 |
| 46 | M | 12.5 | 892 | | 6 | 1.07 | 444 | 158 | 2.46 | 659 | 88 | 2.76 | 406 | 68 | 2.53 |
| 46 | M | 16 | 949 | | 7 | 1.07 | 306.5 | 123 | 2.26 | 499.5 | 163 | 2.53 | 445 | 22 | 2.63 |
| 48 | M | 17 | 1148 | | 8 | 1.07 | 489 | 203 | 2.46 | 360 | 115 | 2.39 | 354.5 | 64 | 2.46 |
| 51 | M | 15 | 289 | | 9 | 1.07 | 1060 | 156 | 2.96 | 494.5 | 169 | 2.51 | 460 | 108 | 2.55 |
| 54 | M | 17.5 | 893 | | 10 | 0.97 | 976 | 239 | 2.87 | 674 | 168 | 2.70 | 561 | 171 | 2.59 |
| 49 | M | 20 | 393a | | | | | | | | | | | | |
| 49 | M | 20 | 393b | | | | | | | | | | | | |
| 53 | M | 60 | 1433 | | 12 | 1.00 | 1162 | 201 | 2.98 | 580 | 148 | 2.64 | 570 | 158 | 2.61 |
| 61 | M | 60 | 77 | | 13 | 1.00 | 531.5 | 155 | 2.58 | 455 | 196 | 2.41 | 594 | 242 | 2.55 |
| 54 | M | 62.5 | 694 | | 14 | 1.03 | 520.5 | 149 | 2.57 | 592 | 150 | 2.65 | 418 | 121 | 2.47 |
| 57 | M | 63 | 1001 | | 15 | 1.07 | 800 | 86 | 2.85 | 400.5 | 149 | 2.40 | 433.5 | 112 | 2.51 |
| 54 | M | 66 | 540 | | 11 | 1.07 | 360.5 | 129 | 2.36 | 370.5 | 120 | 2.40 | 356 | 127 | 2.36 |
| 57 | M | 60 | 1607 | | | | | | | | | | | | |
| 54 | M | 32 | 1191 | | 16 | 1.00 | 558.5 | 170 | 2.59 | 710.5 | 88 | 2.79 | 557 | 93 | 2.67 |
| 56 | M | 30 | 1530 | | 17 | 1.00 | 956.5 | 172 | 2.89 | 667.5 | 190 | 2.68 | 676 | 88 | 2.77 |
| 57 | M | 30 | 663 | | 18 | 1.03 | 675 | 285 | 2.59 | 867.5 | 180 | 2.84 | 572.5 | 202 | 2.57 |
| 57 | M | 30 | 1361 | | 19 | 1.00 | 1316 | 548 | 2.89 | 703.5 | 180 | 2.72 | 633.5 | 87 | 2.74 |
| 53 | M | 90 | 1322 | | 20 | 1.00 | 811 | 251 | 2.75 | 790 | 114 | 2.83 | 734 | 60 | 2.83 |
| 59 | M | 90 | 762 | | 21 | 1.00 | 603 | 333 | 2.43 | 549 | 185 | 2.56 | 469.5 | 130 | 2.53 |
| 60 | M | 92 | 652 | | 22 | 1.07 | 620.5 | 208 | 2.62 | 895 | 139 | 2.88 | 510.5 | 83 | 2.63 |
| 62 | M | 92 | 527 | | 23 | 1.03 | 1136 | 204 | 2.97 | 1102 | 195 | 2.96 | 615 | 65 | 2.74 |
| 64 | M | 87.5 | 1270 | | 24 | 0.97 | 1230 | 109 | 3.05 | 1052 | 193 | 2.93 | 684.5 | 153 | 2.73 |
| 57 | M | 67.5 | 621 | | 25 | 1.03 | 380.5 | 112 | 2.43 | 562.5 | 75 | 2.69 | 452.5 | 127 | 2.51 |
| 57 | M | 70 | 692 | | 26 | 1.03 | 452 | 160 | 2.47 | 523 | 124 | 2.60 | 579 | 113 | 2.67 |
| 57 | M | 70 | 1644 | | 27 | 1.00 | 987 | 303 | 2.84 | 538.5 | 172 | 2.56 | 499 | 206 | 2.47 |

Fig. 4C

| | | | | | | | | | | | | | |
|---|---|---|---|---|---|---|---|---|---|---|---|---|---|
| 743.5 | 119 | 2.80 | 530 | 81 | 2.65 | 79 | 0.85 | | 2.33 | 2.75 | 2.75 | 0.07 | 145 |
| 614 | 133 | 2.68 | 406.5 | 128 | 2.44 | 79 | 0.89 | | 2.38 | 2.68 | 2.50 | 0.11 | 125 |
| 767 | 73 | 2.84 | 522 | 212 | 2.49 | 74 | 0.89 | | 2.16 | 2.67 | 2.67 | 0.14 | 175 |
| 474.5 | 124 | 2.54 | 446.5 | 76 | 2.57 | 84 | 0.81 | | 2.46 | 2.77 | 2.59 | 0.08 | 134 |
| 753 | 248 | 2.70 | 926.5 | 147 | 2.89 | 74 | 0.89 | | 2.30 | 2.76 | 2.85 | 0.09 | 156 |
| 461 | 127 | 2.52 | 363.5 | 105 | 2.41 | 81 | 0.83 | | 2.37 | 2.71 | 2.54 | 0.13 | 109 |
| 299.5 | 251 | 1.69 | 444 | 72 | 2.57 | 76 | 0.87 | | 2.00 | 2.50 | 2.33 | 0.39 | 126 |
| 384.5 | 83 | 2.48 | 502 | 49 | 2.66 | 85 | 0.80 | 2.51 | 2.32 | 2.66 | 2.49 | 0.10 | 103 |
| 405.5 | 180 | 2.35 | 411 | 114 | 2.47 | 76 | 0.87 | | 2.51 | 2.75 | 2.57 | 0.23 | 145 |
| 704.5 | 47 | 2.82 | 729 | 89 | 2.81 | 71 | 0.91 | | 2.28 | 2.67 | 2.76 | 0.11 | 143 |
| | | | | | | 78 | 0.86 | | | | | | |
| | | | | | | 69 | 0.93 | | | | | | |
| | | | | | | 69 | 0.93 | | | | | | |
| 577.5 | 135 | 2.65 | 712.5 | 58 | 2.82 | 71 | 0.91 | | 2.50 | 2.74 | 2.74 | 0.16 | 140 |
| 592 | 286 | 2.49 | 526.5 | 187 | 2.53 | 73 | 0.90 | | 2.25 | 2.51 | 2.51 | 0.06 | 213 |
| 609 | 94 | 2.71 | 495 | 76 | 2.62 | 62 | 0.98 | 2.63 | 2.63 | 2.67 | 2.60 | 0.09 | 118 |
| 453 | 73 | 2.58 | 391.5 | 98 | 2.47 | 78 | 0.86 | | 2.35 | 2.74 | 2.56 | 0.18 | 103.6 |
| 418.5 | 78 | 2.53 | 455 | 111 | 2.54 | 72 | 0.90 | | 2.36 | 2.61 | 2.44 | 0.09 | 113 |
| | | | | | | 44 | 1.13 | | | | | | |
| 532.5 | 69 | 2.67 | 658.5 | 79 | 2.76 | 86 | 0.79 | | 2.14 | 2.70 | 2.70 | 0.08 | 100 |
| 979 | 100 | 2.94 | 724 | 70 | 2.82 | 68 | 0.94 | 2.64 | 2.64 | 2.82 | 2.82 | 0.10 | 124 |
| 918.5 | 86 | 2.92 | 622.5 | 95 | 2.72 | 67 | 0.94 | | 2.64 | 2.80 | 2.73 | 0.15 | 170 |
| 541.5 | 262 | 2.45 | 693 | 160 | 2.73 | 58 | 1.02 | | 2.75 | 2.70 | 2.70 | 0.16 | 247 |
| 726.5 | 134 | 2.77 | 739 | 112 | 2.80 | 71 | 0.91 | | 2.55 | 2.80 | 2.80 | 0.04 | 134 |
| 665 | 156 | 2.71 | 543 | 170 | 2.57 | 61 | 0.99 | | 2.54 | 2.56 | 2.56 | 0.10 | 195 |
| 469.5 | 202 | 2.43 | 386 | 149 | 2.37 | 68 | 0.94 | 2.68 | 2.59 | 2.77 | 2.59 | 0.20 | 156 |
| 500.5 | 97 | 2.61 | 501 | 133 | 2.57 | 67 | 0.94 | | 2.68 | 2.84 | 2.77 | 0.19 | 139 |
| 1001.5 | 149 | 2.93 | 780.5 | 201 | 2.76 | 72 | 0.90 | | 2.52 | 2.79 | 2.88 | 0.13 | 161 |
| 548 | 65 | 2.68 | 468 | 58 | 2.61 | 54 | 1.05 | 2.78 | 2.78 | 2.65 | 2.59 | 0.11 | 87 |
| 545 | 112 | 2.64 | 470 | 110 | 2.56 | 76 | 0.87 | | 2.31 | 2.65 | 2.59 | 0.08 | 124 |
| 630 | 117 | 2.71 | 660 | 72 | 2.77 | 66 | 0.95 | | 2.54 | 2.67 | 2.67 | 0.15 | 174 |

Fig. 4D

| | Sex | Age | ID | # | Marker | Ratio | V1 | V2 | V3 | V4 | V5 | V6 | V7 | V8 | V9 |
|---|---|---|---|---|---|---|---|---|---|---|---|---|---|---|---|
| 57 | M | 105 | 1318 | | | | | | | | | | | | |
| 56 | M | 84 | 1591 | | | | | | | | | | | | |
| 57 | M | 82 | 1679 | 28 | | 1.00 | 1329 | 479 | 2.93 | 886.5 | 225 | 2.82 | 1541.5 | 133 | 3.15 |
| 65 | M | 100 | 1134 | 29 | | 0.97 | 437.5 | 156 | 2.45 | 760.5 | 185 | 2.76 | 656 | 139 | 2.71 |
| 57 | M | 45 | 1639 | 30 | | 1.07 | 584 | 122 | 2.66 | 464.5 | 171 | 2.47 | 438.5 | 112 | 2.51 |
| 60 | M | 45 | 1010 | 31 | | 1.00 | 743.5 | 166 | 2.76 | 1139.5 | 100 | 3.02 | 868 | 165 | 2.85 |
| 58 | M | 75 | 867 | 32 | | 1.00 | 805 | 174 | 2.80 | 1632.5 | 165 | 3.17 | 1969.5 | 272 | 3.23 |
| 58 | M | 76 | 1109 | 33 | | 1.00 | 694.5 | 155 | 2.73 | 630.5 | 153 | 2.68 | 603 | 145 | 2.66 |
| 61 | M | 75 | 960 | 34 | | 1.00 | 401 | 137 | 2.42 | 561 | 185 | 2.57 | 344.5 | 156 | 2.28 |
| 61 | M | 74 | 1154 | 35 | High | 1.07 | 1051.5 | 244 | 2.91 | 1156.5 | 88 | 3.03 | 576 | 210 | 2.56 |
| 59 | M | 64.5 | 1073 | 36 | Apex | 0.97 | 514.5 | 150 | 2.56 | 518.5 | 195 | 2.51 | 616.5 | 187 | 2.63 |
| 61 | M | 55 | 1716b | 37 | | 1.07 | 380 | 127 | 2.40 | 582 | 197 | 2.59 | 531 | 136 | 2.60 |
| 60 | M | 58.5 | 248 | 38 | | 1.07 | 1144.5 | 196 | 2.98 | 806.5 | 153 | 2.82 | 436.5 | 175 | 2.42 |
| 62 | M | 66 | 358 | 39 | | 0.97 | 1164 | 791 | 2.57 | 1397 | 232 | 3.07 | 1102 | 92 | 3.00 |
| 58 | M | 64.5 | 1345 | 40 | | 1.07 | 388 | 77 | 2.49 | 481.5 | 94 | 2.59 | 487 | 213 | 2.44 |
| 64 | M | 66 | 171 | | | | | | | | | | | | |
| 60 | M | 21 | 1199 | 41 | | 1.00 | 470.5 | 147 | 2.51 | 436.5 | 81 | 2.55 | 433 | 198 | 2.37 |
| 60 | M | 20 | 1364 | 42 | | 1.03 | 574 | 191 | 2.58 | 660.5 | 122 | 2.73 | 653 | 182 | 2.67 |
| 61 | M | 20 | 1105 | 43 | | 1.00 | 855 | 226 | 2.80 | 582 | 245 | 2.53 | 498 | 147 | 2.55 |
| 61 | M | 21 | 1331 | 44 | | 1.00 | 538 | 102 | 2.64 | 520.5 | 181 | 2.53 | 456 | 102 | 2.55 |
| 62 | M | 21 | 1416 | | | | | | | | | | | | |
| 60 | M | 60 | 1206 | | | | | | | | | | | | |
| 61 | M | 55 | 1716a | | | | | | | | | | | | |

| | | | | | | | | | | | | | |
|---|---|---|---|---|---|---|---|---|---|---|---|---|---|
| 62 | M | 60 | 858 | 45 | | 1.07 | 687 | 107 | 2.76 | 371 | 139 | 2.37 | 375 | 120 | 2.41 |
| 62 | M | 31.25 | 1365 | | | | | | | | | | | |
| 64 | M | 33 | 910 | 46 | | 1.00 | 692.5 | 132 | 2.75 | 813 | 65 | 2.87 | 781.5 | 157 | 2.80 |
| 66 | M | 35 | 759 | 47 | | 1.03 | 390.5 | 154 | 2.37 | 494 | 146 | 2.54 | 510 | 67 | 2.65 |
| 67 | M | 37 | 1682 | 48 | | 0.97 | 1333 | 265 | 3.03 | 1303.5 | 291 | 3.01 | 814.5 | 101 | 2.85 |
| 64 | M | 3 | 830 | 49 | | 1.03 | 403.5 | 120 | 2.45 | 543 | 112 | 2.63 | 399.5 | 169 | 2.36 |
| 64 | M | 2 | 1115 | 50 | | 1.07 | 434.5 | 122 | 2.49 | 461 | 145 | 2.50 | 389 | 97 | 2.47 |
| 64 | M | 5 | 979 | 51 | | 1.07 | 574 | 225 | 2.54 | 555 | 142 | 2.62 | 512 | 91 | 2.62 |
| 64 | M | 75 | 926 | 52 | | 1.00 | 764 | 165 | 2.78 | 701.5 | 129 | 2.76 | 454 | 117 | 2.53 |
| 66 | M | 75 | 1254 | 53 | | 1.00 | 497 | 187 | 2.49 | 644.5 | 218 | 2.63 | 578.5 | 153 | 2.63 |
| 68 | M | 72 | 235 | 54 | | 1.07 | 509 | 130 | 2.58 | 563 | 70 | 2.69 | 527 | 207 | 2.51 |
| 65 | M | 60 | 1310 | 55 | | 1.00 | 708.5 | 165 | 2.74 | 535 | 186 | 2.54 | 530.5 | 228 | 2.48 |
| 67 | M | 60 | 780 | 56 | | 1.00 | 706 | 246 | 2.66 | 2127.5 | 391 | 3.24 | 701 | 276 | 2.63 |
| 69 | M | 60 | 161 | 57 | | 1.07 | 421.5 | 140 | 2.45 | 475.5 | 108 | 2.57 | 412.5 | 78 | 2.52 |
| 61 | M | 61.5 | 1531 | 58 | | 1.00 | 540.5 | 120 | 2.62 | 690.5 | 164 | 2.72 | 619.5 | 182 | 2.64 |
| 74 | M | 60 | 1259 | 59 | | 1.00 | 829.5 | 146 | 2.83 | 685 | 199 | 2.69 | 577.5 | 147 | 2.63 |
| 76 | M | 60 | 795 | 60 | | 1.03 | 1019 | 161 | 2.93 | 537 | 150 | 2.59 | 630.5 | 131 | 2.70 |
| 66 | M | 82 | 102 | 61 | | 1.00 | 1716 | 387 | 3.12 | 776.5 | 288 | 2.69 | 611 | 51 | 2.75 |
| 70 | M | 76.5 | 1385 | 62 | | 1.00 | 958.5 | 154 | 2.91 | 630.5 | 150 | 2.68 | 666.5 | 200 | 2.67 |
| 72 | M | 75 | 1084 | 63 | | 1.07 | 397.5 | 135 | 2.42 | 467.5 | 35 | 2.64 | 427 | 125 | 2.48 |
| 74 | M | 75 | 532 | 64 | | 1.00 | 671.5 | 182 | 2.69 | 594 | 110 | 2.68 | 858.5 | 95 | 2.88 |
| 79 | M | 65 | 1572 | | | | | | | | | | | |
| 80 | M | 68.75 | 984a | 65 | | 1.07 | 279 | 180 | 2.00 | 393 | 113 | 2.45 | 354 | 126 | 2.36 |
| 80 | M | 50 | 1076 | | | | | | | | | | | |
| 82 | M | 68.75 | 984b | | | | | | | | | | | |
| 60.3544 | | 53.33 | | 79 | | | 317 | | 2.5011 | | | | | |

Cornell Partsolids

| | | | | | | | | | | | | | |
|---|---|---|---|---|---|---|---|---|---|---|---|---|---|
| 45 | F | | SM0070 | 1 | 1.06 | 440 | 101 | 2.53 | 573 | 32 | 2.73 | 518.5 | 73 | 2.65 |
| | | | SM0055 | 2 | | | | | | | | | | |
| 45 | F | | SL0074 | 3 | 1.06 | 1043 | 198 | 2.93 | 891 | 82 | 2.91 | 394 | 77 | 2.50 |

GiveAScan

| | | | | | | | | | | | | | |
|---|---|---|---|---|---|---|---|---|---|---|---|---|---|
| 62 | F | 0 | P0006 | 1 | 1.20 | 174.5 | 42 | 2.12 | 981.5 | 22 | 2.98 | 747 | 4.8 | 2.87 |

METHOD AND SYSTEM FOR MEASURING LUNG TISSUE DAMAGE AND DISEASE RISK

CROSS REFERENCE TO RELATED APPLICATIONS

This application is a continuation-in-part of PCT/US09/34021 filed 13 Feb. 2009 claiming priority under 35 USC 120, which claims priority under 35 USC 119(e) to U.S. 61/099,564 filed 23 Sep. 2008, U.S. 61/047,841 filed 23 Apr. 2008, U.S. 61/044,411 filed 11 Apr. 2008, and U.S. 61/028,504 filed 13 Feb. 2008, the entire contents of each of which are incorporated herein by reference in their entirety.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

REFERENCE TO A SEQUENCE LISTING

Not applicable.

BACKGROUND

1. Field of the Invention

This invention relates to a system, software, and method for quantitatively measuring lung tissue damage, esp. regional or lobe damage, by measuring the mineral density deviations and/or mineral composition deviations from normal in a CT scan combined with measurements of airflow lung function measurements. This can be used in measuring lung exposure, damage, disease risk, and response to therapy using radiological techniques in combination with data analysis. The methods described here can also be applied to other diseases that involve mineralization including COPD, esophageal cancer, cardiovascular diseases, and osteoarthritis.

2. Background of the Invention

According to the National Cancer Institute, the number of new cases of lung cancer in 2007 (both non-small cell and small cell combined) is estimated to be 213,380, and the number of deaths is estimated to be 160,390. There currently is no reliable method for measuring an individual's lung damage and risk for developing lung cancer. Lung cancer screening trials rely on age and individual reported exposure to cigarette smoke and other carcinogens to identify a high risk screening population. This method of lung cancer risk assessment provides a crude estimate of carcinogenic exposure and does not take into account (a) the damage the specific individual has sustained as a result of a wide range of potential lung tissue insults and (b) the variation in individual response to the exposure. An objective method for measuring the amount of lung tissue damage an individual has sustained would be of great benefit to effectively monitor and manage lung cancer risk groups and personalize disease monitoring and treatment of lung cancer patients.

Computed tomography scanning technology has improved dramatically in the last 10 years. Most health care institutions in the United States are now able to routinely obtain thin slice CT scans of the entire lung within a few seconds. The detailed x-ray attenuation measurements these scans produce have the potential to reveal important information relating to the progression and management of lung cancer, chronic obstructive pulmonary disease (COPD), and other smoking related diseases. Numerous studies have revealed important CT imaging features that provide important clinical information that is now important to the early management of thoracic diseases. Thin slice CT allowed for the differentiation of part-solid lung lesions, which must be managed more aggressively due to their high probability of malignancy when detected at baseline. In addition, high resolution CT measurements of airway wall thickness and the extent of emphysema is providing new insight into the management of COPD.

The fields of environmental health and aerosol sciences have also studied the fundamental mechanisms leading to lung cancer. These studies have found that the deposition of particulate matter in the lung, as occurs when smoking, has particular patterns of distribution. Of particular importance is the analysis of air flow patterns in human airways. Several studies have shown that certain structures in the airways, particularly the carinal ridge at airway bifurcations, receive significantly more particulate deposition than other locations in the lung. Smoking population studies have further revealed that for some exposures airway branching levels above three or four receive significantly more particulate load than other airway regions. It is these high exposure locations that both receive a disproportionate amount of particulate load and have the potential to provide an early indication of the level of damage sustained throughout the rest of the lung.

It is further well known that airways contain large amounts of hyaline cartilage which has the property that it mineralizes, i.e. calcifies, with various forms of repeated stress and age.

BRIEF SUMMARY OF THE INVENTION

In a preferred embodiment, there is provided a method of using a computer processor to receive data representing lung X-ray images of an individual, using said data to calculate an X-ray attenuation score from one or more measurements of a density deviation at one or more airway bifurcation locations compared to a density value at a region surrounding the bifurcation, combining the X-ray attenuation score with a lung function score of the individual calculated from one or more lung function measurement tests selected from the group consisting of a CT lung function analysis, a spirometry test, a lung ventilation scan, a lung perfusion scan, and a pH value from an exhaled breath condensate test, wherein said combined X-ray attenuation score and lung function score provides an assessment of the individual against a lung disease risk index.

The method may include wherein the spirometry test is FEV1/FVC.

The method may further include wherein the CT lung function analysis includes a CT wall thickness measurement, emphysema measurement, or both.

The method may also include wherein the X-ray attenuation score is obtained from an imaging modality selected from the group consisting of a CT scan, chest X-ray, digital radiography, X-ray tomosynthesis, and computer aided X-ray radiography.

The method also contemplates wherein the density deviation is a measurement of calcification, particle deposition, ossification, or combinations thereof.

The method may also include the steps of measuring over time the lung disease risk index and establishing a disease trajectory for the individual, and/or may include the steps of measuring over time the CT lung function scan and establishing a disease trajectory for the individual.

The method may also include wherein the CT lung function scan includes measurements of a shape change in the one or more bifurcations comprising a thickening of the lung tissue at the bifurcation or surrounding tissue, or a loss of tissue or hole in the lung tissue at the bifurcation or surrounding tissue.

The method may also include wherein measuring density deviations further comprises measuring the sum of the logs of maximum HU density deviations from nearby low exposure regions along the airway tree in a CT scan.

The method may also include wherein the lung disease risk index is a lung cancer risk index.

The method may also include the step of identifying locations that represent high lung cancer risk.

The method may also include the step of identifying specific lung regions or lobes that represent high lung cancer risk by calculating a region-specific or lobe-specific lung cancer risk index by combining a region-specific X-ray attenuation score with a region-specific lung function score, wherein the region-specific X-ray attenuation score is obtained by applying a lung region-specific classifier to the X-ray attenuation score to identify lung region-specific data subsets of bifurcation locations, and the region-specific lung function score is obtained by modifying the lung function score based upon factors affecting regional airflow.

In another preferred embodiment, there is provided a method for preparing a data set that provides an estimation of a patient's lung cancer risk, comprising:
(i) obtaining a measurement of the pH of the lung using an exhaled breath condensate (EBC) device;
(ii) obtaining results of a pulmonary function test obtained by spirometry;
(iii) obtaining a measurement of the level of X-ray attenuation in the airways and calculating a bifurcation damage index (BDI); and,
(iv) combining the pH, spirometry, and X-ray attenuation into a single lung cancer risk index.

This method may include the step of applying a classifier to the distribution of measurements to separate lung cancer risk levels and patient sub-populations, COPD patient populations, individuals at risk and patients having other pulmonary related diseases.

In yet another preferred embodiment, there is provided an imaging system for lung disease, comprising: an X-ray imaging modality; and a computer programmed to: receive data representing lung X-ray images of an individual, using said data to calculate an X-ray attenuation score from one or more measurements of a density deviation at one or more airway bifurcation locations compared to a density value at a region surrounding the bifurcation, combining the X-ray attenuation score with a lung function score of the individual calculated from one or more lung function measurement tests selected from the group consisting of a CT lung function analysis, a spirometry test, a lung ventilation scan, a lung perfusion scan, and a pH value from an exhaled breath condensate test, wherein said combined X-ray attenuation score and lung function score provides an assessment of the individual against a lung disease risk index.

The imaging system may include wherein the imaging modality is selected from the group consisting of a CT scan, chest X-ray, digital radiography, X-ray tomosynthesis, and computer aided X-ray radiography.

The imaging system may include wherein the density deviation is a measurement of calcification, particle deposition, ossification, or combinations thereof The imaging system may include wherein the imaging modality is a multiple energy CT scan and provides features to further distinguish individual response to exposure.

The imaging system may include wherein the computer is programmed to compare changes between one or more assessments of lung cancer risk index.

The imaging system may include wherein combining measurements into a lung cancer risk index further comprises adjusting the metric for additional clinical data such as age, gender, smoking history, comorbidity, and family history.

In another preferred embodiment, there is provided a computer program product, directly loadable into the RAM of a digital computer, comprising software code portions for implementing the steps of the method as set forth herein, when said product is run on said digital computer.

The computer program product may also include wherein the software code portions are downloadable from a network.

The computer program product may also include wherein the software code portions are encoded on a portable computer-readable medium The invention described here also provides a method of quantitatively measuring lung cancer risk by measuring the mineral density deviations and/or mineral composition deviations from normal or less stressed region in a CT scan. Since mineralization is a common response to stress across many tissues in the human body, such as ligaments, tendons, vascular tissues, and the various forms of cartilage, the methods herein may be used to measure damage and risk and have applicability to other diseases including COPD, esophageal cancer, cardiovascular diseases, aging of ligaments and tendons, and osteoarthritis.

In another preferred embodiment, the invention includes a method of quantitatively measuring lung tissue damage, comprising the steps of i) obtaining a high resolution CT lung scan of an individual; ii) analyzing the CT scan and measuring density deviations of airway tissue locations having the highest particle deposition, wherein the density deviations are obtained using either airway geometry analysis or fluid flow analysis; iii) measuring the subjects local and/or global degree of airway obstruction (e.g. FEV1/FVC is a global lung function measurement and CT wall thickness and emphysema measurements are local) and v) combining any or all of these measurements into a lung disease risk index.

In preferred embodiments, the method includes (a) wherein analyzing the CT scan and measuring density deviations further comprises measuring the sum of the logs of maximum HU density deviations from nearby low exposure regions along the airway tree in a CT scan; or (b) wherein the location of highest particle deposition comprise one or more bifurcation locations or curved regions, and wherein the step of combining the measurements further comprises placing a greater influence over the measurement of lung damage from the one or more bifurcation locations or curved regions; or (c) wherein the CT scan is a multiple energy CT scan and provides features to further distinguish individual response to exposure; or (d) where it further comprises the step of comparing changes between one or more assessments of lung cancer risk index, and using said comparison to determine a measured response to therapy; or (e) wherein combining measurements into a lung cancer risk index further comprises adjusting the metric for additional clinical data such as age, gender, smoking history, comorbidity, and family history, as is other important diagnostic tests; and/or (f) wherein combining measurements into a lung cancer risk index further comprises adding other CT analysis data to the metric such as COPD wall thickness and emphysema score as both are measures of pulmonary obstruction which is correlated strongly with lung cancer.

In one preferred embodiment, the therapy is lung cancer therapy.

In another preferred embodiment, the density and composition CT measurements are taken from hyaline cartilage tissue located at the articular surface of a bone, and can be further used to provide therapeutic and/or clinical information regarding osteoarthritis of an individual. Accounting for and subtracting the mineralization response of non-disease related processes and utilizing a model of mineralization damage response (e.g. exponential mineralization in response to damage requires a log function to estimate tissue damage) will thus reveal the damage and risk level of osteoarthritis.

In another preferred embodiment, the density and composition CT measurements are taken from vascular wall regions and adjacent areas and can be further used to provide therapeutic and/or clinical information regarding cardiovascular disease of an individual. Accounting for and subtracting the mineralization response of non-disease related processes and utilizing a model of mineralization damage response (e.g. exponential mineralization in response to damage requires a log function to estimate tissue damage) will thus reveal the damage and risk level of cardiovascular disease including Coronary Artery Disease.

In another preferred embodiment, the density and composition CT measurements are taken from ligaments and tendons in order to damage and risk of failure. Accounting for and subtracting the mineralization response of non-disease related processes and utilizing a model of mineralization damage response (e.g. exponential mineralization in response to damage requires a log function to estimate tissue damage) will thus reveal the damage and risk level of tissue failure including knee ligament risk of injury.

The invention described herein also provides a system for quantitatively measuring lung tissue damage by measuring the mineral density deviations and/or mineral composition deviations from normal in a CT scan at high exposure locations such as the Hyaline cartilage found at bifurcations and airway cartilage rings and combining this with lung function information, such as FEV1 and FVC.

In another preferred embodiment, the invention provides a system for quantitatively measuring lung tissue damage, comprising: i) means for obtaining a high resolution CT scan of lung tissue of an individual; ii) means for analyzing the CT scan and measuring density deviations of airway tissue locations having the highest particle deposition, wherein the density deviations are obtained using either airway geometry analysis or fluid flow analysis; and iii) means for combining measurements into a lung cancer risk index.

In another preferred embodiment the measurement of the shape of the bifurcation and surrounding tissues is also used to model risk. Deviations in the ideal shape of a bifurcation, such as thickening of the bifurcation, and any loss of tissue near the bifurcation (e.g. holes) are measured and provide additional information on the stress of the airway tissues at and around bifurcation regions. Variations in airway shape can serve to provide evidence of increased stress, or provide evidence of a future increase or decrease in the focal deposition of particulate matter and each of these provides further refinement on lung cancer risk. A decrease in risk can occur if a variation in shape serves to more evenly distribute particulate matter and therefore toxic dose on the respiratory epithelium.

In another preferred embodiment additional information on the lung environment is used to compute lung cancer risk at each location throughout the lung. Information on the amount of ventilation, perfusion, pH, and other lung characteristics are combined with spirometry measurements, such as FEV1/FVC, and image measurements, such as Bifurcation Damage Index (BDI) and regional emphysema, to determine lung cancer risk at each location in the lung. Ventilation decreases in the apex and increases in the base of the lung, so a gradient of FEV1/FVC values can be constructed throughout the lung. Ventilation is further compromised near regions of emphysema and the regional impact on FEV1/FVC can be estimated. Measurement of calcification is modulated by the variation of pH at different locations in the lung and the size, or the generation of the bifurcation, of the airways structures being measured allowing for measurement of calcification damage, or BDI, attained in each region of the lung. Analysis of the combination of these and other characteristics permits lung cancer risk estimation at each location in the lung. 3D analysis of change in risk over time can be used to identify regions at high risk for developing lung cancer. Regional calculation of risk and/or its change over time can be used to predict the location of a future lung cancer and inform risk mitigation and lung cancer therapy planning strategies.

Measurement of the pH of the lung, which can be obtained using Exhaled Breath Condensate (EBC) capturing devices, is an established method for determining inflammatory and other forms of stress and damage in the lung and has been found to be both robust and reproducible [Vaughn2003]. Higher lung acidity has been found in persons with compromised lung function including lung cancer, COPD, and asthma [Chan2009, Kostikas2002, Koczulla2009, Borrill2008]. Higher lung acidity has also been found in smokers versus non-smokers [Boulet2006]. It is also established that higher lung acidity inhibits the formation of airway calcification [Chan2002]. Thus the degree of calcification in the lung, either across the whole lung or measured regionally, is likely rising only to the maximum degree that the lung environment will support.

In another preferred embodiment, an estimate of individual lung cancer risk is obtained by analyzing the measurement of the pH of the lung, as may be obtained using an EBC device, and the measurement of the level of calcification in the airways, such as the BDI.

In another preferred embodiment, an estimate of the individual lung cancer risk is obtained by analyzing the measurement of the pH of the lung, as may be obtained using an EBC device, the measurement results of a pulmonary function test such as can be obtained by spirometry, and the measurement of the level of X-ray attenuation in the airways, such as the Bifurcation Damage Index (BDI). Applying a classifier to the distribution of measurements has the potential to better separate lung cancer risk levels and patient sub-populations, COPD patient populations, and individuals at risk and having other pulmonary related diseases.

In preferred embodiments, the system includes (a) wherein means for analyzing the CT scan and measuring density deviations further comprises means for measuring the average deviation in HU density along the airway tree in a CT scan; or (b) wherein the location of highest particle deposition comprise one or more bifurcation locations or curved regions, and wherein the means for combining the measurements further comprises a means for placing a greater influence over the measurement of lung damage from the one or more bifurcation locations or curved regions; or (c) wherein the CT scan is a multiple energy CT scan and provides material composition features to further distinguish individual response to exposure; (d) further comprising means for comparing changes between one or more assessments of lung cancer risk index, and using said comparison to determine a measured response to therapy; (e) wherein the means for combining measurements into a lung cancer risk index further comprises means for adjusting the metric for additional clinical data such as age, gender, smoking history, comorbidity, and family history, as is other important diagnostic tests; and/or (f) wherein means for combining measurements into a lung cancer risk index further comprises means for adding other CT analysis data to the metric such as COPD wall thickness and emphysema score as both are correlated strongly with lung cancer.

In one preferred system, the therapy is lung cancer therapy.

In another preferred system, the density and composition CT measurements are taken from hyaline cartilage tissue located at the articular surface of a bone, and can be further used to provide therapeutic and/or clinical information regarding osteoarthritis of an individual.

In another preferred embodiment all regions of the lung are analyzed with a computer program to identify dangerous combinations of obstruction and calcification/particle deposition/mineralization. Locations of partial or complete obstruction in the airway and the parenchyma (e.g. Bullae) are detected and the physician is notified. This information can be used to determine if a surgical or therapeutic intervention is necessary to reduce the risk of developing lung cancer and other diseases.

In another preferred embodiment the patterns of mineralization found at bifurcations are analyzed to provide information on the type and extent of particulate exposure including the mass, shape, and charge of the particle that caused the damage to the lung.

In another preferred embodiment the lung cancer risk index is used to create a personalized lung cancer screening protocol that optimizes the number of visits, the radiation dose, screening cost, and cancer detection rate. A baseline CT scan combined with FEV1/FVC data is combined to form the LCRI and follow-up screening plans are then calculated to verify the projected risk of the patient over time. Since obstruction and mineralization change slowly, the frequency and duration of screening can be optimized to the individual. It should be possible to perform some follow-up screening visits for low baseline risk patients by measuring lung function (FEV1/FVC) more often than a full high resolution CT scan, thereby reducing the cost and dose required for lung cancer screening.

In another preferred embodiment, the LCRI is combined with measurements and attributes of a suspected lung cancer lesion to determine the probability of malignancy of the lesion. This is useful to establish before performing a potentially dangerous needle biopsy.

In another preferred embodiment a surgical planning tool analyzes lung tissue calcification/particle deposition/mineralization and potential resection and interventional options to provide the surgeon with the best therapeutic method for ensuring that lung cancer and other disease risk is minimized. This could advise on the lung cancer risk associated with each of several therapeutic options.

The invention described herein also provides a computer program product, directly loadable into the RAM of a digital computer, comprising software code portions for implementing the steps of the method(s) as set forth herein, when said product is run on said digital computer.

In preferred embodiments, the software code portions are downloadable from a network.

BRIEF DESCRIPTION OF THE DRAWINGS

FIG. 1 shows details of a bifurcation measurement method.

FIGS. 4A-4H is a spreadsheet of individual patient data, their CT measurements, lung function measurements, measurement correction values, and a calculated lung cancer risk index. FIG. 4 extends over eight pages in landscape page orientation. The data reported here provides evidence that careful measurement of mineral deposits at airway locations combined with a measurement of airway obstruction can provide a metric for determining an individual patient's lung cancer risk status.

FIG. 5 shows the damage index plotted against the patient's age. FIG. 4(a) shows that a lung cancer risk threshold can be established, from which diagnostic and therapeutic determinations can be made.

FIG. 6 shows frequency plotted against the lung cancer risk index (LCRI). FIG. 6 shows that the cancer and the normal populations show separation along the index.

FIG. 7 shows that mineralization measurements can assist in determinations of osteoarthritis.

FIG. 8 shows that mineralization occurs in G.I. tissues, e.g. esophagus, and can assist in determinations of gastrointestinal conditions, such as cancer, GERD, Barrett's, etc. where tissue damage has resulted in increased mineralization.

FIG. 9 shows the cancer regression line used to establish the LCRI.

FIG. 10 shows the age and pack year distribution.

FIG. 12 shows the difference between the control groups and the cancer groups.

FIG. 13 also shows cancer data points against a range of controls from 10-29 PY, 30-49 PY, 50-69 PY, and >70 PY.

DETAILED DESCRIPTION OF THE INVENTION

Definitions

Figure 1:
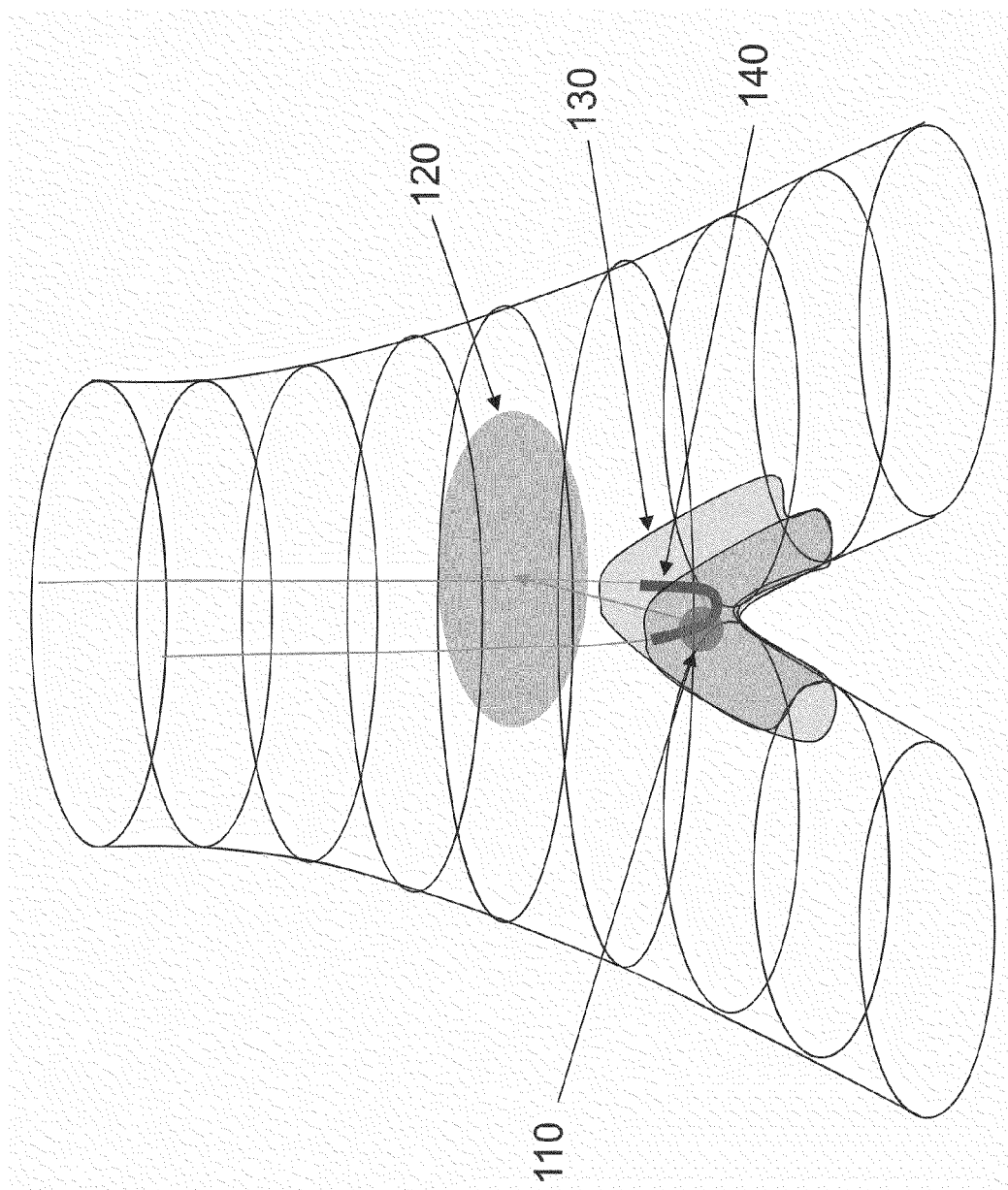
FIG. 1 is a representative drawing of an airway bifurcation.

The following definitions are provided as an aid to understanding the detailed description of the present invention.

The term AIRWAY refers to those parts of the respiratory system through which air flows, to get from the external environment to the alveoli. The airway begins at the mouth or nose, and accesses the trachea via the pharynx. The trachea branches into the left and right main bronchi at the carina, situated at the level of the second thoracic vertebra. The bronchi branch into large bronchioles, one for each lobe of the lung. Within the lobes, the bronchi further subdivide some 20 times, ending in clusters of alveoli.

The term BDI refers to Bifurcation Damage Index (BDI) and is a method which uses a CT scanner (X-ray attenuation) to compare the tissue density from particle/calcification/mineralization at an airway bifurcation against the density at nearby tissue, and assessing the damage to the bifurcation tissue. Additional details are disclosed below.

The term CT refers to computed tomography, a medical imaging method that uses tomography, or radiologic sectioning, created by computer processing. By processing a large number of digital two-dimensional images, a three-dimensional image may be obtained.

The term EBC refers to Exhaled Breath Condensate and is used to describe the collected bodily fluid from an EBC device which measures in a patient's airway the pH, volatile compounds, non-volatile compounds, proteins, etc.

The term FEV1 refers to "Forced Exhaled Volume in 1 second" and is a frequently used lung function index in spirometry for assessing airway obstruction.

The term FVC refers to "Forced expiratory Vital Capacity" (sometimes FEVC), and is another lung function index used in spirometry for assessing lung function. FVC is the volume change of the lung between full inspiration to total lung capacity and a maximal expiration to residual volume.

The term GI refers to the gastrointestinal tract and includes the tongue, mouth, esophagus, stomach, small intestine, large intestine, and colon.

GLOBAL LUNG FUNCTION MEASUREMENT, as used herein, refers in a preferred embodiment, to a ratio of Forced Expiratory Volume in one second to Forced Vital Capacity (FEV1/FVC). However, Global Lung Function measurement may also in some embodiments include other lung function studies, including, without limitation, Vital Capacity (VC), Inspiratory Vital Capacity (IVC), Expiratory Vital Capacity (EVC), Forced Inspiratory Vital Capacity (FIVC), Forced Inspiratory Volume in one second (FIV1), Peak Expiratory Flow (PEF), Maximal Expiratory Flow (MEF), Forced Expiratory Flow (FEF), Maximal Inspiratory Flow (MIF), Reserve Volume (RV), Functional Residual Capacity (FRC), and Total Lung Capacity (TLC), alone, in combinations, or as ratios.

The term HYALINE CARTILAGE refers to a protective matrix found within an individual at locations involving movement of body parts, i.e. respiratory system, joints, etc. It contains no nerves or blood vessels, and its structure is relatively simple. Except where it coats the articular ends of bones, it is covered externally by a fibrous membrane, the perichondrium. This membrane contains vessels that provide the cartilage with nutrition. If a thin slice is examined under the microscope, it will be found to consist of cells of a rounded or bluntly angular form, lying in groups of two or more in a granular or almost homogeneous matrix. The cells, when arranged in groups of two or more, have generally straight outlines where they are in contact with each other, and in the rest of their circumference are rounded. They consist of clear translucent protoplasm in which fine interlacing filaments and minute granules are sometimes present; embedded in this are one or two round nuclei, having the usual intranuclear network. The cells are contained in cavities in the matrix, called cartilage lacunae; around these the matrix is arranged in concentric lines, as if it had been formed in successive portions around the cartilage cells. This constitutes the so-called capsule of the space. Each lacuna is generally occupied by a single cell, but during the division of the cells it may contain two, four, or eight cells. Hyaline cartilage also contains chondrocytes which are cartilage cells that produce the matrix. Hyaline cartilage matrix is mostly made up of type II collagen and Chondroitin sulfate, both of which are also found in elastic cartilage.

The term X-RAY IMAGING MODALITY refers to radiographic techniques that provide X-ray attenuation data, especially from the lung. Specific modalities include, without limitation, CT scan, chest X-ray, digital radiography, X-ray tomosynthesis, and computer aided X-ray radiography. X-ray attenuation, as described herein, refers to the change in X-ray data and imaging as a result of lung calcification, ossification, and/or particulate deposition within the lung.

The term LOCAL LUNG ENVIRONMENT refers to data associated with a CT lung tissue measurement, emphysema score, lung ventilation scan, lung perfusion scan, and/or lung pH measurement.

The terms LUNG PERFUSION SCAN and LUNG VENTILATION SCAN refer to nuclear medicine tests that produce a picture of lung function. A lung perfusion scan produces a picture of blood flow to the lungs. A lung ventilation scan measures the ability of the lungs to take in air and uses radiopharmaceuticals to produce a picture of how air is distributed in the lungs.

The term LUNG CANCER RISK INDEX is addressed below. The impact of small carcinogenic particles on lung tissue has been extensively studied over the last decade. Numerous studies have reported that the flow of air in the airways results in certain airway locations receiving a disproportionate deposition of particulate matter. In particular, bifurcation locations in the airway tree receive significantly more particulate deposits and, when the deposits are damaging to tissue, also sustain some of the greatest damage in the lung. The cumulative result of this damage can result in lung cancer forming preferentially in the locations that receive the greatest particle deposition load.

Measurement of airway bifurcations in CT scans is difficult due to the rapid decrease in airway size as branching progresses. The size of a bifurcation region between two airway branches quickly reduces to less than the size of CT scanner Point Spread Function (PSF) at a certain branching level. Without the use of advanced CT analysis methods, the CT density of bifurcations is only able to be reliably measured at the first few, i.e 3 to 4 airway branching levels. Manual measurement of maximum CT density at seven branching locations was performed to estimate lung cancer risk. A Lung Cancer Risk Index (LCRI) is performed by measuring the average density deviation of a plurality of bifurcation regions in the airways. At each bifurcation the log of the maximum CT density minus the average density of a low stress cartilage region near the bifurcation (ie. Log(bifurcation−comparison) is performed. A log function is used to estimate the damage associated with an exponential calcification response. The subtraction of a comparison region measurement is performed in order to remove the influence of other calcification processes that can occur in the bifurcation region such as a global increase in calcification or a widespread influence of mechanical stress. The selection of the comparison region should be made to avoid locations in the airway that have a propensity not to calcify. This includes regions that are near large moving structures such as the esophagus, the heart or the aorta that can potentially palpate the cartilage and inhibit calcification. A more advanced method for measuring the comparison region would track the average density of cartilage rings above and below the bifurcation and spatially estimate the comparison densities across the bifurcation, if not the entire airway tree. The measurement of maximum density at a bifurcation was performed by identifying two 26 connected voxels in the bifurcation region that produced the largest average CT density. Orthogonal reformatting of the CT scan is permitted in order to enable the review of maximum calcification in all dimensions, but is not strictly required. The two pixel requirement was used in order to set a size threshold for a focal increase in CT density and to help combat the influence of scanner noise. This is particularly important when large patients are scanned at low dose. The LCRI may also be used to establish threshold values for diagnostic and therapeutic determinations, as described further herein.

The term OSTEOARTHRITIS refers to an inflammatory joint disorder characterized by the breakdown and eventual loss of the cartilage in a joint.

Description of the Figures

Airway Bifurcations

Referring now to the figures, FIG. 1 is a representative drawing of an airway bifurcation. FIG. 1 shows details of a bifurcation measurement method. FIG. 1 shows the expected particle deposition load at the location of an airway bifurcation as shown.

Computed Tomography (CT) scans are able to obtain high resolution images of the human airway and provide detailed measurements of X-ray density (expressed as Hounsfield Units or HU) along the entire airway lumen and surrounding tissues. Given the preferential carcinogen load that certain airway regions receive, particularly airway bifurcations 130, as is illustrated in FIG. 1, it is reasonable to expect that these regions will exhibit changes from normal tissue, 120. It is further expected that early changes in these locations will represent an early indication of lung cancer risk well before changes are visible in other lung areas. It is also possible that the increased calcification is in part due to the sequestration of carcinogens and other substances that are harmful and need to eventually be cleared from the lungs.

An analysis of high resolution CT scans of individuals with high exposure to cigarette smoke reveals that the CT density of bifurcation and other high curvature regions in the airways appears to increase. The method shown in FIG. 1 includes determining the maximum intensity region in the bifurcation region(s) 110 and subtracting the comparison intensity 120. The comparison region 120 is a region of the airway, i.e the cartilage rings, from which measurements are taken to compare against the measurements at the carinal ridge 140, i.e. the area of the bifurcation having the maximum exposure/mineralization. The comparison intensity is the measurement taken from the comparison region 120.

Figure 2:
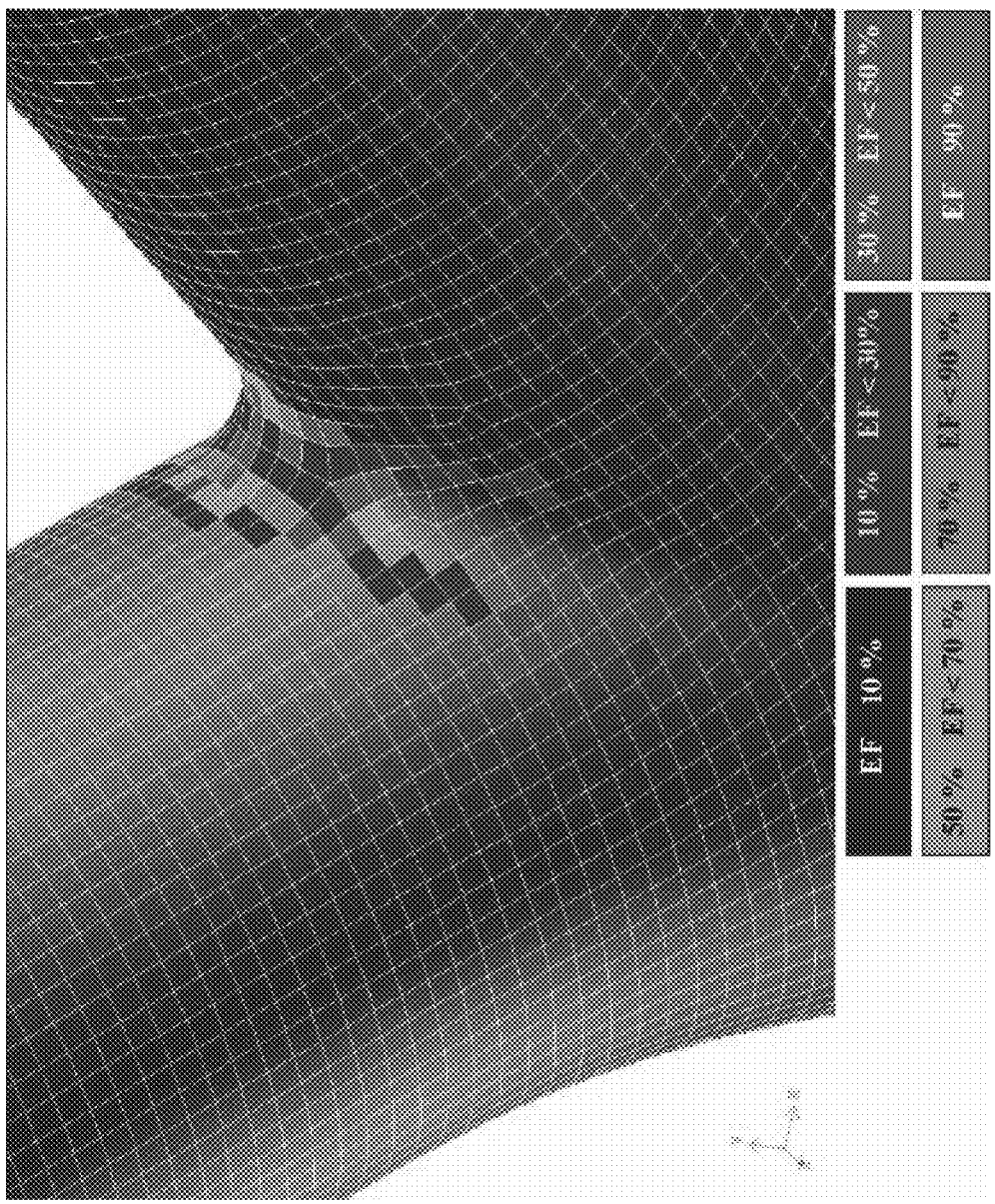
FIG. 2 is a simulation showing the enhancement of particle deposition at a bifurcation location.

FIG. 2 is a computational fluid dynamics (CFD) simulation showing the enhancement of particle deposition at a bifurcation location.

Figure 3:
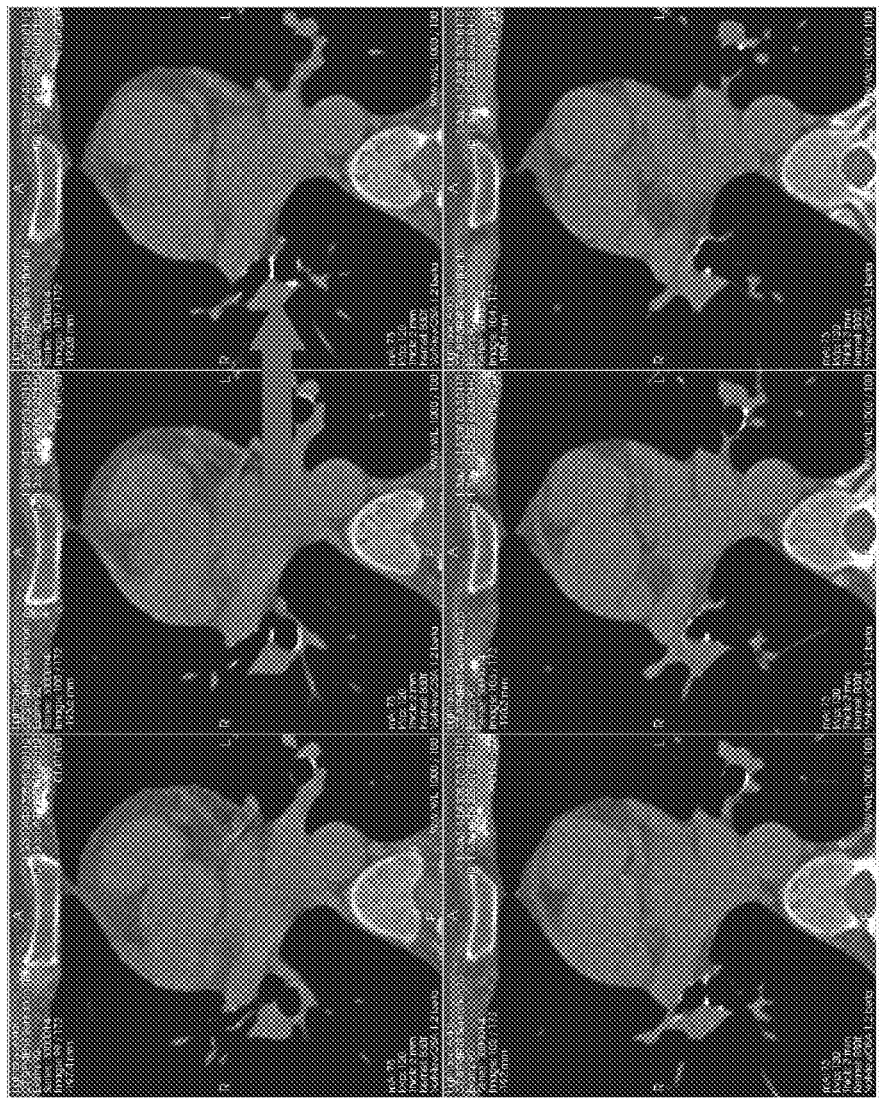
FIG. 3 is a panel of CT images showing significant calcification at a bifurcation.

FIG. 3 shows slices from a high resolution CT scan of an individual with a high CT density response at bifurcation locations as described in particle flow studies. Analysis of several smoker CT scans shows generally a less intense, but clear density increase. The arrow indicates where, on the CT scan, that significant calcification has been determined to exist.

Further to this, publications on the deposition of asbestos fibers also point out the higher level of exposure sustained at the location of airway bifurcations [3].

One important feature of the invention is the use of measurements of the increases of x-ray density at bifurcation locations (and other high exposure areas) using more recently available CT scans with sufficient resolution to assess lung tissue damage in CT images, and by other imaging methods.

Airway Inflammatory Processes

Without being held to one particular theory, the mechanism by which damage translates into higher density is likely related to continuous inflammatory response of the affected tissues. Hyaline cartilage, which is the type that is a major component of the human airway, is known to mineralize or ossify with repeated stress and age. In addition, the Interleukin-6 and Interleukin-7 pathways represent a potential mechanism by which a repeated inflammatory response could result in increased calcification and CT density. The inflammation pathway is implicated in smoking and asbestos exposure suggesting a common pathway toward increased density.

Lung Cancer Risk Index—Part 1: Lung Function Measurements

Spirometry, or measuring the breath, includes a number of traditional pulmonary function tests for assessing lung health and/or diseases. FEV1 refers to the PFT which measures the volume of air forced out during exhalation by a patient in 1 second. FEV1 is frequently used as a lung function index in spirometry for assessing airway obstruction.

FVC refers to "Forced expiratory Vital Capacity" (sometimes FEVC), and is another lung function index used in spirometry for assessing lung function. FVC is the volume change of the lung between full inspiration to total lung capacity and a maximal expiration to residual volume.

When measuring the Global Lung Function, in a preferred embodiment, a ratio of FEV1/FVC is obtained. The ratio in healthy adults should be approximately 75-80%. In obstructive diseases, FEV1 is reduced, resulting in a lower ratio, e.g. ~45%.

Lung Cancer Risk Index—Part 2: CT Scan Data

In one preferred embodiment, the invention is to quantitatively measure deviations in CT density at the locations of highest particle deposition. One embodiment of the invention is to analyze a CT scan of the lung and extract the full airway tree down to the limits of detection. A complete analysis of density deviations (from all other potential sources of cartilage mineralization) can be done to determine the overall individual response to all forms of exposure. Modeling and subtraction of various forms of biological stress (e.g. renal issues), biomechanical stress, and all forms of particulate deposition stress can be performed and help understand the type and extent of lung risk and injury. A further analysis can be performed by measuring the locations of highest particle deposition, using either airway geometry analysis or fluid flow analysis. Once this has been done, the measurements can be combined into a global or local lung tissue exposure response score. Additional analysis of airway shape and texture can be performed throughout the airway and an overall lung cancer risk score can be formed by combining this information with standard airway function tests and emphysema scoring methods. Scanning with a multi energy CT scanner should reveal additional information regarding the composition of minerals in the damaged areas. This should provide additional classifications of damage response that could potentially provide additional information on the amount of lung cancer risk and provide guidance on the best methods of treatment. A further refinement of the approach is to measure deviations from age and gender matched control group. This would be necessary if there is a natural increase in density as a result of normal aging.

Another use of the method is to measure the response of an individual to therapy or chemoprevention. A decrease in CT density at these preferential locations or increase in lung function could signal early response to treatment and potentially predict continued treatment response.

CT Measurement Data of Individual Patients

Figure 4F:
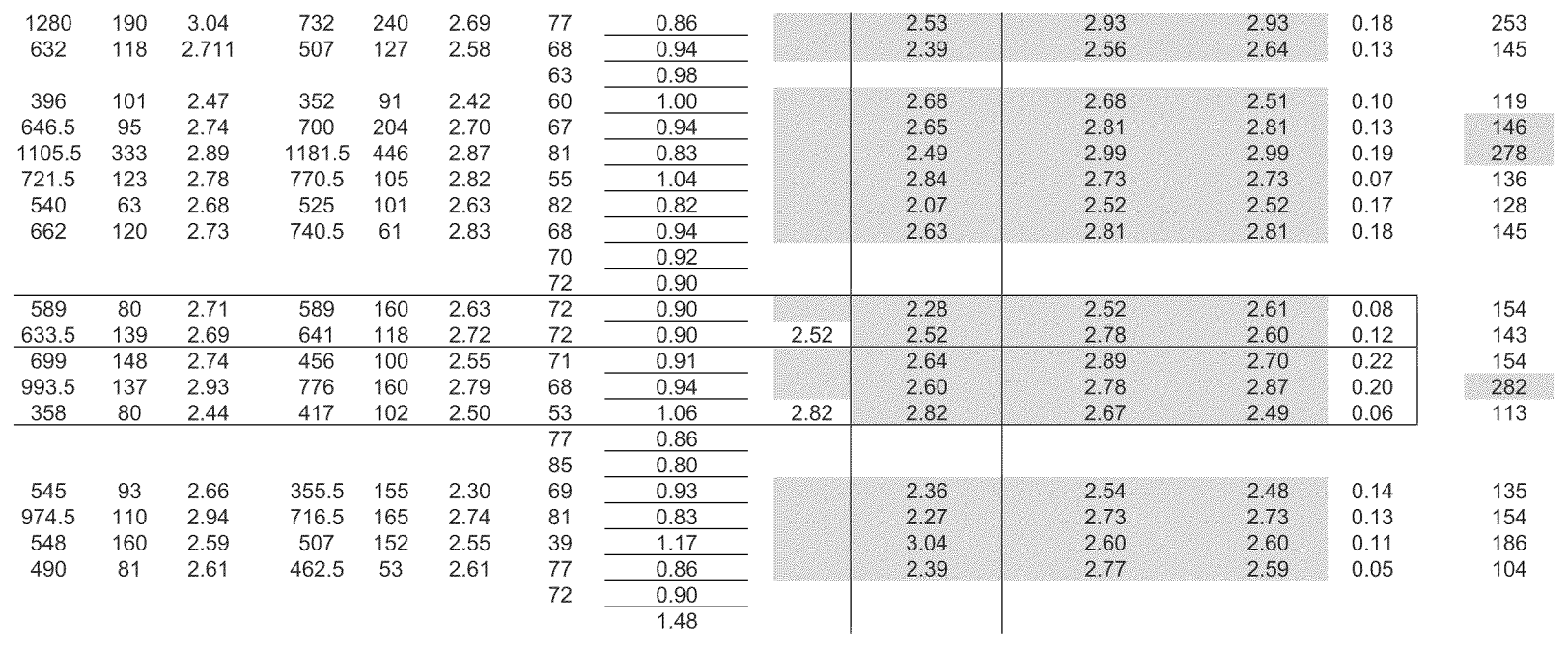
Figure 4H:
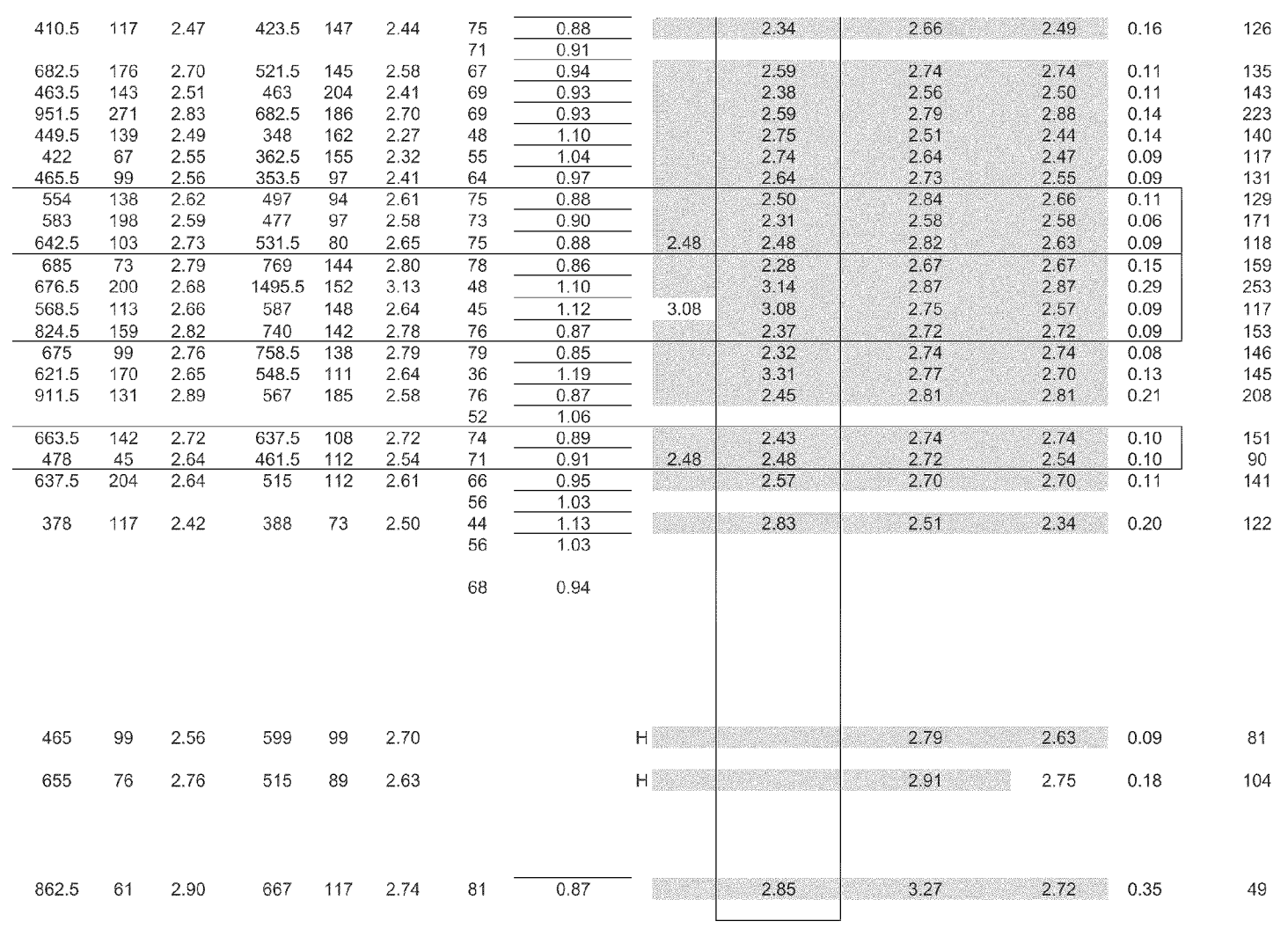

FIG. 4 is a spreadsheet of individual patient data, their CT measurements, lung function measurements, measurement correction values, and a calculated lung cancer risk index. The data reported here provides evidence that careful measurement of mineral deposits at airway locations combined with a measurement of airway obstruction can provide a metric for determining an individual patient's lung cancer risk status. FIG. 4 shows the pack-years, gender, age, and thickness of subjects that were measured with the lung cancer risk index. This is followed by a individual sample identifier and quantitative measurement data from the main bifurcation location of the lung.

FIG. 4 spreadsheet also shows data from the RIGHT bifurcation location, and the LEFT bifurcation location, respectively.

FIG. 4 shows the statistical summaries of the findings, and illustrates the connection between high exposure areas (particulate deposition) and lung disease.

Referring now to the data obtained in FIG. 4, the minimal set of steps needed for a preferred embodiment of the invention is:

(1) Obtain a high resolution scan of an airway tree (CT scan is much preferred).

(2) Track the airway tree in the scanned images and identify bifurcation locations in the airway that have the most particulate deposition (high exposure areas).

(3) Take measurements of CT density (expressed in Hounsfield units) at each of the high exposure areas and combine the measurements to form an overall lung cancer risk index.

In another preferred embodiment, the invention comprises obtaining data. For example in FIG. 4 the spreadsheet data was obtained by specific steps, namely:

(1) Obtain a high resolution 3D CT scan of an airway tree that has the following properties:

(a) No greater than 2 mm slice thickness (about 0.5 mm is the best commercially available and is preferred)

(b) Reconstruction kernels should neither perform too much smoothing or sharpening. Bone kernel is preferred for GE scanners.

(c) Pixel spacing in Z should be no greater than slice thickness (d) Pixel spacing in X and Y should be about 0.8 mm or less we need the best sampling of the airway tree we can get (and slightly oversampled in the Nyquist sense is preferred).

(e) The tube current of the scanner (expressed as mA) should be set high enough that image noise is kept to a reasonable level. Higher mA is preferred.

(2) Track the airway tree in the scanned images and identify locations in the airway that have the most particulate deposition (high exposure areas).

(a) Inspect and find the bifurcation locations in the airway tree by looking through the stack of CT slices using a medical image viewer that supports orthogonal reformats. The Window/Level image viewing parameters were set to 1500 and −100 respectively.

(b) Geometric modeling methods (e.g. 3D Hessian to identify local shape or skeletonization methods) to automatically track the airway tree and identify the bifurcation locations are contemplated as within the scope of the invention.

(3) Take measurements of CT density (expressed in Hounsfield units) at each of the high exposure areas and combine the measurements to form an overall lung cancer risk index.

(a) Inspect each bifurcation area (which is a wedge-like geometry), including the regions on either side of the wedge and moving up the airway. A 2 voxel region was placed on the location in the bifurcation area that would produce the largest average CT density across both voxels. The connected voxels were required to share a vertex or an edge. A 2 voxel area was chosen so that the measurement would be less susceptible to noise and would obtain a measurement of significant airway damage in a focal area.

(b) Measure the average CT density of cartilage directly above or below the bifurcation (measurement of a cartilage ring spanning ¼ of the circumference of the airway is sufficient) and subtract this from the 2 voxel bifurcation value. The log of the resulting value is used to estimate a damage measurement at the bifurcation.

(c) A total of 5 bifurcation measurements were taken per individual including 1 for the main airway bifurcation and 2 for the left airway and 2 for the right airway.

(d) All 5 measurements are averaged to form the average amount of damage sustained by the bifurcations in the lung.

(e) The average of the damage values in the lung are combined with a patients FEV1/FVC ratio to form an overall lung cancer risk index. Higher FEV1/FVC ratios (likely representing higher air velocity and therefore greater focal deposition) require greater amounts of mineralization for the subject to be considered high for lung cancer risk. A simple classifier (e.g. linear or polynomial) is sufficient to assign risk for individuals with FEV1/FVC lung function.

There is a preferred region to take this measurement which is at the periphery of the bifurcation wedge (but the maximum densities may not be in this region, so only taking the measurements there could be problematic). Think of the wedge as getting wider at each end, similar to a saddle for a horse. Each wider end of the bifurcation is the preferred region to take the measurement. The reason this site is better is that the region receives some of the highest exposures and is thick enough to be able to get a good measurement. Very thin walled structures in the middle of the wedge have their CT densities diminished greatly by partial volume artifact, a well understood problem in scanning systems. Also contemplated as within the scope of the invention is taking into account the partial volume artifact and quantitatively estimating what the CT density had to have been to produce the lower densities we see at the thin bifurcation zones. The contribution of air to the convolution of the scanner PSF and the bifurcation tissue can be estimated and corrected.

Another preferred embodiment includes performing a flow analysis of the individual's airway tree and either (a) determining the particle deposition load at each of the maximum CT density locations identified above or (b) measuring the density at the places of highest particle load. The particle deposition amount is then used to weight the individual density measurements. Similarly, we know that partial volume artifact reduces CT density measurements, so we weight each measurement based on the size of the airway being measured. Combining both flow analysis and CT scanning physics (i.e. accounting for partial volume artifact, noise, etc) is a good approach for this measurement problem.

Another preferred embodiment includes analyzing patterns of mineralization to estimate the mass, shape, and charge of the particles that damaged the lung. Higher mass particles will create more focal areas of mineralization at bifurcation locations. For example, asbestos fibers tend to settle in the lower lobes of the lungs due to the influence of gravity.

Another preferred embodiment includes creating a personalized lung cancer screening protocol based on the key components of the lung cancer risk index. Measurement of FEV1/FVC can be used for low risk patients to obtain their expected risk trajectory and status over several years and this can be used to reduce the number and coverage of CT scans.

Another preferred embodiment includes measuring the probability of malignancy of a lung cancer lesion based on a combination of lesion attributes and the lung cancer risk index, including global and local indices.

Finally, a variant of this method could be applied to other organ systems that operate through the use of flowing liquids, air/gas, or solid/liquid mixtures, such as in the case of the digestive track or the lymphatic system.

LCRI vs. Age

Figure 5:
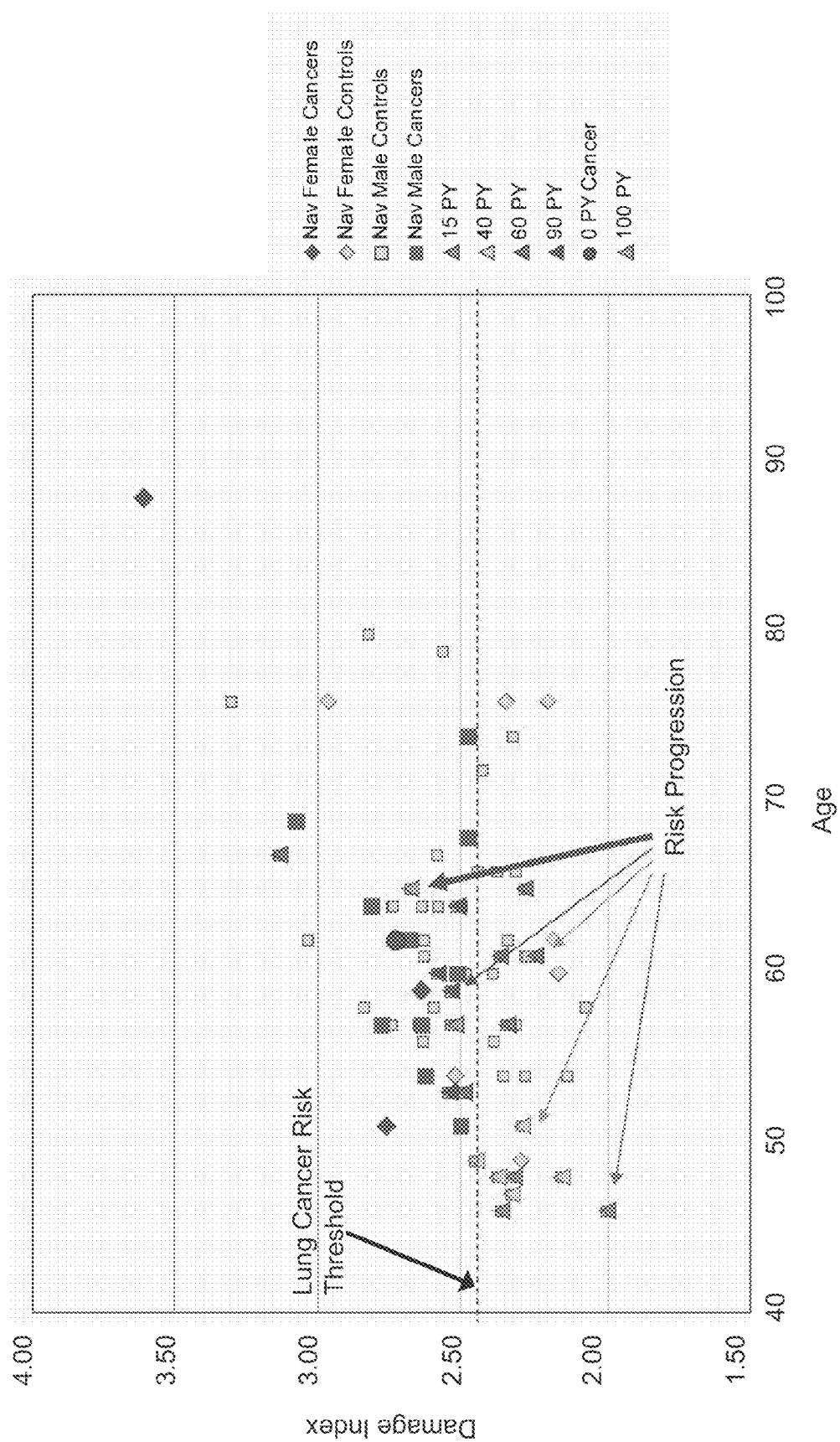
FIG. 5 is a graph of lung cancer risk index results.

FIG. 5 is a graph of lung cancer risk index results and shows the damage index plotted against the patient's age. FIG. 5 shows that a lung cancer risk threshold can be established, from which diagnostic and therapeutic determinations can be made.

FIG. 5 shows female cancers against female controls, and male cancers against male controls. FIG. 5 also shows the risk progression of 15 pack-year to 40 pack-year, to 60 pack-year, to 90 pack-year, to 100 pack-year patients. Within this progression, a lung cancer risk threshold can be determined. Thus, for example, an individual patient's position can be determined on this progression. Thus, a 47-old moving from LCRI of 2.0 to 2.4 over the course of a five year period has a high probability of developing cancer. Given the position and trajectory of an individual, a physician can advise the patient on therapies, detection strategies, and behaviors to reduce their probability of developing cancer, and increase the probability of detecting it at an early stage.

Figure 6:
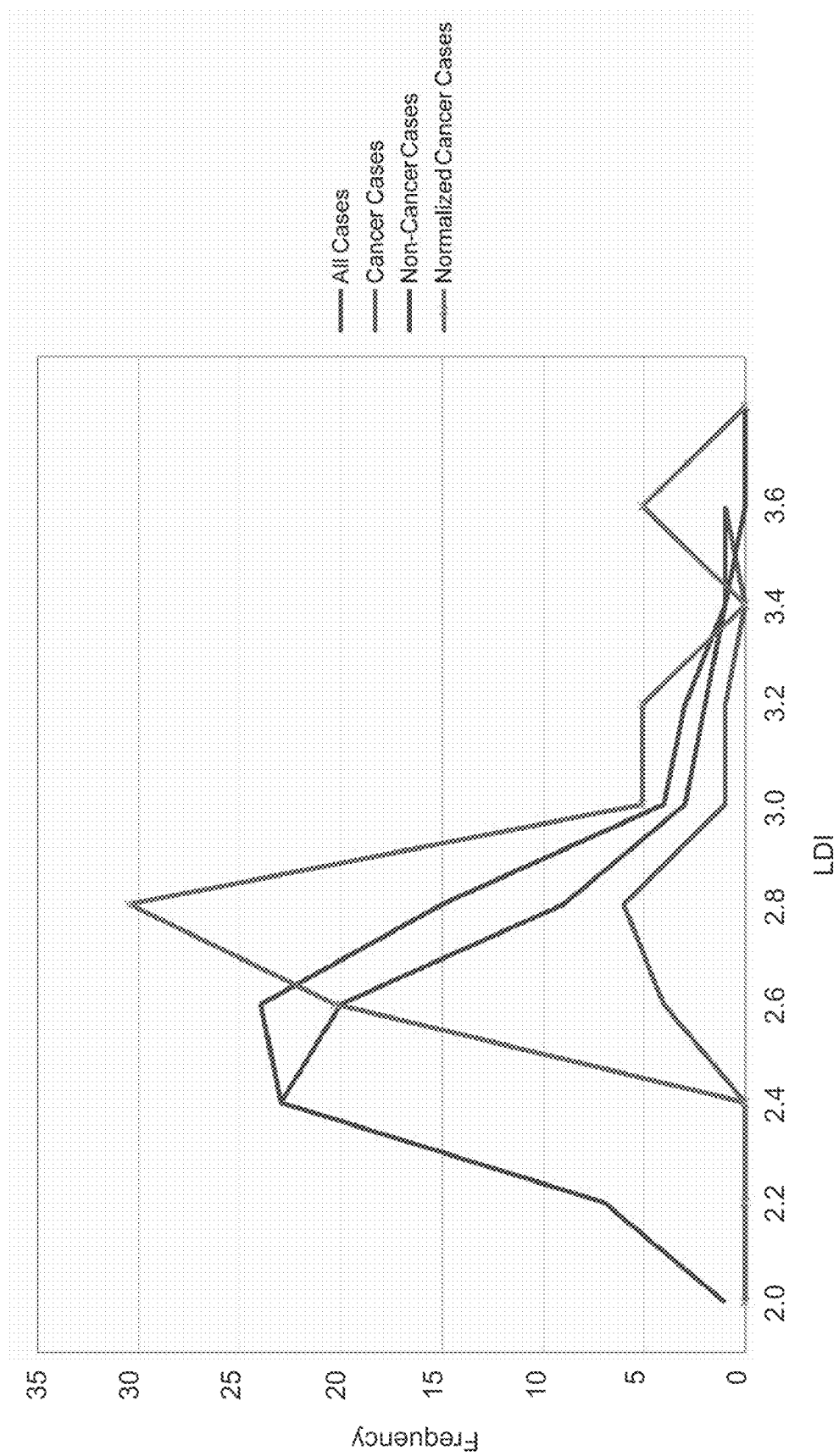
FIG. 6 is a graph of LCRI risk distribution.

FIG. 6 is a histogram of LCRI risk distribution. FIG. 6 shows frequency plotted against the lung cancer risk index (LCRI), and shows that the cancer and the normal populations show separation along the index. FIG. 6 shows the cancer patient LCRI distribution is higher than the control PCRI distribution, taking into account that they have matched with control subjects with roughly the same age, gender, and Pack-Year characteristics. This separation takes into account the normal, biomechanical mineralization processes. Drawing a vertical line at 2.6 yields a sensitivity of 69% and specificity of 77%, yielding a valuable diagnostic test.

CT Measurement of Knee Cartilage

Figure 7:
FIG. 7 is a CT scan of a knee where average CT density of the cartilage is measured.

Referring now to FIG. 7, a CT scan of a knee is shown. Using high resolution, the CT will provide both information about mineral density and composition. The results of this analysis, when compared to average, or normal, mineral densities or compositions, provides essential information concerning inflammation and osteoarthritis of the knee, and for other joints of the body as well.

From the CT scan of a knee and from measuring the average CT density of the cartilage, and hyaline in particular, it provides the ability to measure increased mineral density and mineral composition with high resolution CT, note that osteophytes or bone spurs tend to form in high inflammation areas of the knee: see e.g. MayoClinic.com on bone spurs, causes.

Of course, hyaline cartilage is the most common form of cartilage and changes in its mineral composition and density could serve many purposes including use as an early biomarker of disease and potentially used to measure therapy response.

Hyaline cartilage and other structures (ligaments and tendons) respond to stress and aging by ossifying (increasing minerals). In most people this is a natural and regular process that also includes reducing water content and other things that could change CT density measurements.

There are locations throughout our body that give a natural and measurable response to aging. When we stress those areas more, such as particle deposition at bifurcations in the lung and subsequent inflammation, the tissue mineralizes faster. It also likely adds different kinds of minerals depending on the type of damage and stress and the microenvironment.

It is also considered that carcinogenic or toxic compounds are sequestered within the mineralization of these tissues. This appears to be a highly common mechanism in the body, and our ability to measure it can be used to measure a very wide range of diseases and processes in the body.

The impact of hazardous substances and irritants on the lung can result in several different types of diseases. This includes multiple forms of Chronic Obstructive Pulmonary Disease (COPD), lung cancer, and cardiac conditions. Tracking the path of an individual through the various lung risk features we are capable of measuring (image based features and pulmonary function tests) is useful in understanding the type and severity of disease(s) the individual currently has or is likely to attain at a time in the future. For example, an individual that has rapidly increasing mineralization at airway bifurcations but relatively little loss in pulmonary function will more likely be stricken with lung cancer than COPD.

It is particularly useful to decompose each of the main components of risk, obstruction and deposition/mineralization, into different subtypes. Airway obstruction can be caused by (a) airway wall thickening, (b) emphysema (both of which can be measured in CT), or (c) other factors. Pulmonary function tests consist of many different types and measurements that can further be used to understand the type of obstruction and functional issues occurring in the lung.

Mineralization measurements can be decomposed into the (a) overall airway mineralization, (b) measurement of the degree of calcification at the bifurcation, or (c) different patterns of calcification throughout the lung. In particular, mineralization patterns around bifurcation and their global distribution can tell us a lot about the carcinogen/irritant and the body's reaction to it. For example, larger asbestos particles will undergo sedimentation and tend to form at the base of the lung due to the effect of gravity. Dual energy CT information will further tell us more about the type of carcinogen/irritant and the individual's reaction to it.

Mapping the position and trajectory of an individual through each of these measurements over time will give useful information on the types of disease the individual currently has and is likely to face in the future. This would be highly useful in managing and treating patients for lung cancer, COPD, and other respiratory diseases. This information may also be useful (alone or in combination with additional cardiac measurements) in understanding the current status and future status of cardiac diseases and cardiac function.

Measurement Methods, Locations, and Uses

Methods are contemplated herein for measurement of aging at several sites across the body using this process. CT is one way to measure it, but biopsies and other scanning methods could also be used for these diagnostic tests. There appears to be support for measuring many diseases including the following.

Lung Cancer:

Measure the bifurcations and other locations and measure the amount and rate of mineralization. This appears to be correlated with lung cancer.

Osteoarthritis:

Measure small changes in mineral content of the hyaline cartilage at joint and other locations since literature that supports an ossifying process in articular/hyaline cartilage. Osteoarthritis (OA) is a chronic inflammatory disease characterized by progressive deterioration of articular cartilage in synovial joints. It is the leading cause of disability for individuals over the age of 65, and can become very painful. Risk factors include aging, obesity and overuse or abuse of joints. Although, the exact biological mechanism responsible for the onset of OA is unknown, it is generally accepted that OA, at least in the advanced phase of the disease, results from reactivation of endochondral ossification, (see e.g. http://www-.peprotech.com/content/focusarticles.htm?id=72, incorporated by reference herein in its entirety for any teachings necessary for a fuller understanding of the invention by a person of ordinary skill in the art).

And literature supports that immobilization of a limb (causes stress on cartilage) will cause increased mineralization that can be measured with CT. Torelli et al. disclose that computed tomography (CT) is an accurate examination technique for osteoarthritis lesions, which most frequently involve the knee, (see Torelli Braz J Med Biol res April 2004 Vol 37(4) 493-501, incorporated by reference herein in its entirety for any teachings necessary for a fuller understanding of the invention by a person of ordinary skill in the art).

Another article describes the ability measure mineralization in micro-CT. Batiste et al. disclose that 3-D MRI and micro-CT data formats made it possible to quantify cartilage damage, joint-space, and osseous changes in the rabbit ACLT model of Osteo-Arthritis, (see e.g. Batiste et al. Osteoarthritis and Cartilage, Vol. 12, Issue 8 Aug. 2004, pp. 614-626, incorporated by reference herein in its entirety for any teachings necessary for a fuller understanding of the invention by a person of ordinary skill in the art).

It appears that studying osteoarthritis, and specifically, the subtle mineralization processes occurring in cartilage processes provide for the determination of deviations from normal, and which provides a viable way to measure disease, progression, and therapy response.

Cardiac and Vascular Disease:

It is also contemplated to be able to determine the natural mineralization process of vascular and cardiac tissues to measure subtle changes there, especially locations where hyaline cartilage is involved.

Gastrointestinal Tract

It appears that the esophagus/digestive track is also another site we can measure stress through quantification of mineralization. Bertram et al. disclose that mineralization, esp. focal deposits of calcification of the GI tissues is observed, including tongue, the gastric mucosa and blood vessels of the stomach, the small and large intestine. Bertram et al., 1996, Guides for Toxicologic Pathology, incorporated by reference herein in its entirety for any teachings necessary for a fuller understanding of the invention by a person of ordinary skill in the art. This can be observed in a similar manner as that described herein for analyzing CT cases for lung.

Figure 8:
FIG. 8 is a CT scan of an esophagus where increased mineralization is present.

FIG. 8 shows an image of an example of esophageal calcification. The red contour shows the site of calcification. FIG. 8 is a CT scan of an esophagus where average CT density of the cartilage is measured. FIG. 8 shows that mineralization detection can assist in determinations of gastrointestinal conditions, including cancer, GERD, Barrett's, and so forth, where tissue damage has resulted in increased mineralization.

CT Imaging and Diagnostic Systems

In another embodiment, a system is provided which includes a medical imaging device known in the art for generating a plurality of images, specifically a computed tomography (CT) system.

During a CT imaging session, an individual lies horizontal and is exposed to a plurality of x-rays measured with a series of X-ray detectors. A beam of x-rays passes through a particular thin cross-section or "slice" of the individual. The detectors measure the amount of transmitted radiation. This information is used to compute the x-ray attention coefficient for sample points in the body. A gray scale image is then constructed based upon the calculated x-ray attenuation coefficients. The shades of gray in the image contrast the amount of x-ray absorption of every point within the slice. The slices obtained during a CT session can be reconstructed to provide an anatomically correct representation of the area of interest within the body that has been exposed to the x-rays.

Once initial CT images have been obtained, the images are generally segmented. The segmentation process classifies the pixels or voxels of an image into a certain number of classes that are homogeneous with respect to some characteristic (i.e. intensity, texture, etc.). For example, in a segmented image of the brain, the material of the brain can be categorized into three classes: gray matter, white matter, and cerebrospinal fluid. Individual colors can be used to mark regions of each class after the segmentation has been completed. Once the segmented image is developed, surgeons can use the segmented images to plan surgical techniques.

CT Imaging Steps

Generally, creating a segmented CT image involves several steps. A data set is created by capturing CT slices of data. Through the segmentation process, a gray scale value is then assigned to each point in the data set and different types of tissues will have different gray scale values. Each type of material in the data is assigned a specific value and, therefore, each occurrence of that material has the same gray scale value. For example, all occurrences of bone in a particular image may appear in a particular shade of light gray. This standard of coloring allows the individual viewing the image to easily understand the objects being represented in the images.

One embodiment of a medical imaging system includes a CT imaging device or scanner, a processor and an interface unit. The CT imaging device generates a plurality of image data sets. In the context of CT, acquisition of image data is generally referred to as "scans". A processor is configured to perform computations in accordance with embodiments of the present invention and is also configured to perform computation and control functions for well-known image processing techniques such as reconstruction, image data memory storage, segmentation and the like. The processor may comprise a central processing unit (CPU) such as a single integrated circuit, such as a microprocessor, or may comprise any suitable number of integrated circuit devices and/or circuit boards working in cooperation to accomplish the functions of a central processing unit. The processor desirably includes memory. Memory within the processor may comprise any type of memory known to those skilled in the art. This includes Dynamic Random Access Memory (DRAM), Static RAM (SRAM), flash memory, cache memory, etc. The memory may be a single type of memory component or may be composed of many different types of memory components. The processor is also capable of executing the programs contained in memory and acting in response to those programs or other activities that may occur in the course of image acquisition and image viewing. As used herein, "adapted to", "configured" and the like refer to mechanical or structural connections between elements to allow the elements to cooperate to provide a described effect; these terms also refer to operation capabilities of electrical elements such as analog or digital computers or application specific devices (such as an application specific integrated circuit (ASIC)) that are programmed to perform a sequel to provide an output in response to given input signals.

An interface unit is coupled to the processor and is adapted to allow human users to communicate with system. The processor is further adapted to perform computations that are transmitted to the interface unit in a coherent manner such that a human user is capable of interpreting the transmitted information. Transmitted information may include images in 2D or 3D, color and gray scale images, and text messages regarding diagnosis and detection information. The interface unit may be a personal computer, an image work station, a hand held image display unit or any convention image display platform generally grouped as part of a CT system.

All data gathered from multiple scans of the individual is to be considered one data set. Each data set can be broken up into smaller units, either pixels or voxels. When the data set is two-dimensional, the image is made up of units called pixels. A pixel is a point in two-dimensional space that can be referenced using two dimensional coordinates, usually x and y. Each pixel in an image is surrounded by eight other pixels, the nine pixels forming a three-by-three square. These eight other pixels, which surround the center pixel, are considered the eight-connected neighbors of the center pixel. When the data set is three-dimensional, the image is displayed in units called voxels. A voxel is a point in three-dimensional space that can be referenced using three-dimensional coordinates, usually x, y and z. Each voxel is surrounded by twenty-six other voxels. These twenty-six voxels can be considered the twenty-six connected neighbors of the original voxel.

In an embodiment of the present invention, a computer-aided system for use in the diagnosis and detection of disease comprises an image acquisition device for acquiring a plurality of image data sets and a processor adapted to classify selected tissue types within the image data sets based on a hierarchy of signal and anatomical models. The processor is further adapted to differentiate anatomical context of the classified tissue types for use in the diagnosis and detection of a selected disease. The system further comprises an interface unit for presenting the classified tissue types within the image data sets and anatomical context of the classified tissue types for aiding an interpretation of the processed image data sets. The anatomical models are parametric, mathematical representations of anatomical tissues. The anatomical context comprises at least one of lung nodules indicative of lung cancer, healthy lung tissue, diseased lung tissue indicative of chronic obstructive pulmonary disease (COPD) and other pathological descriptions of tissue that can be characterized by radiologists and further modeled mathematically.

In an exemplary embodiment, the imaging device is a x-ray CT scanner. A CT system is particularly well adapted to acquire a plurality of images, or alternatively slices, of a region of interest. Also, in this exemplary embodiment, the imaging object is a lung.

Example—A Quantitative Method for Estimating Lung Cancer Risk

Referring back to FIG. 9, in this example, the performance of a novel method for estimating individual lung cancer risk is evaluated based on the combined measurement of CT calcification density at airway bifurcations and FEV1/FVC.

Thirteen early lung cancer patients were selected from a CT screening study based on the availability of low dose, whole lung CT data with <=1.25 mm slice thickness and good image quality. 91 cancer-free control subjects were also selected with these criteria plus the requirement that each subject's age was within +/−10 years and pack years was within +/−10 years of a cancer case. 7/13 (54%) cancer positive and 70/91 (77%) cancer negative scans were performed with 1.0 mm slice thickness. 2 cancer cases and 14 control cases were female. Siemens scanners and the B60f reconstruction kernel were used, except for 2 control cases that used the B80f kernel. Pulmonary function tests were administered at CT scan time according to ATS spirometry guidelines. A quantitative method was developed to calculate a lung cancer risk index (LCRI) based on airway bifurcation CT density and FEV1/FVC. A single reader manually performed all CT image measurements.

LCRI measurement of all 104 cases achieved a lung cancer detection sensitivity and specificity of 69% and 79%, respectively. Mean LCRI values for 10-29, 30-49, 50-69, and >=70 pack years controls were 2.34, 2.46, 2.60, and 2.59, respectively. 54/91 (59%) control cases had an LCRI value below the lowest cancer positive LCRI value. This increased to 55/74 (74%) when applied to the subset of cases where FEV1/FVC was above 50% and CT slice thickness was 1.0 mm.

Example—Bifurcation Damage Measurement Method

Each HRCT scan was measured using a medical data review application (VolView 3.0) with standard image review features. To maintain measurement consistency a window/level setting of 1500 and −100 was used to review each dataset.

The main tracheal bifurcation was measured and a visual search was performed on axial slices for two bifurcations in each lung exhibiting maximal calcification. Thus 5 bifurcations were measured in each patient. The two 26-connected voxels with the greatest CT density either along the carinal ridge or a small downstream region were averaged to form a starting Bifurcation Density (BD). Two voxels were averaged to avoid image noise biases. A search for evidence of cartilage rings just above the bifurcation was performed and the average density of a representative region of cartilage roughly spanning ¼ the circumference of the airway was measured. This average density will be referred to as the Comparison Density (CD). Care was taken during the measurement of CD to avoid partial volume artifacts and other factors that influence calcification (e.g. The posterior half of the trachea has a tendency not to calcify). The CD value was subtracted from the BD value in order to remove the influence of factors not related to focal PM deposition. A log function was then applied to the (BD-CD) value in order to reflect the amount of damage the tissue sustained. This was in part driven by the literature on biological calcification, which describes calcification as a crystal growth process that can progress rapidly in response to small changes in the tissue microenvironment. The mean value of all five bifurcations was computed and a final constant scanner Correction Factor (CF) was applied to account for varying scanner types and protocols. This mean value after correction is referred to as the Bifurcation Damage Index (BDI) and was used to estimate the individual's lung cancer risk. The BDI calculation is summarized by the equation in Table 1.

Example—Scanner Correction Factors

In this example, scanner correction factors were constructed based on an analysis of the mean BDI values for 69 control subjects that were scanned with at least 1.25 mm slice thickness. The correction factors in Table 1 are used to account for partial volume artifact on the Siemens scanners used herein It is also recognized that more robust forms of scanner calibration may be used, including a method that leverages phantom analysis and accounts for scanner Point Spread Function (PSF) as well as the orientation of the bifurcation with respect to CT slices.

$$BDI = \frac{CF}{n} \cdot \sum_{i=1}^{n} \log(BDi - CDi) \quad (1)$$

TABLE 1

SCANNER CORRECTION FACTORS

| Scanner Model | Slice Thickness | Correction |
|---|---|---|
| Definition | 1.00 mm | 0.9676 |
| Sensation 64 | 1.00 mm | 1.0000 |
| Volume Zoom | 1.00 mm | 1.0264 |
| Volume Zoom | 1.25 mm | 1.0703 |

Example—Bronchiole & Alveolar Damage Measurement

This example discloses a method for estimating lung cancer risk and requires that FEV1 and FVC scores are obtained near the time of the HRCT scan. It is particularly important that these respiratory maneuvers are performed according to ATS guidelines for performing spirometry measurements, including supervision by trained personnel. The ratio of FEV1/FVC, a commonly used metric for assessing respiratory health, was used to estimate lung cancer risk. No corrections were made to the FEV1/FVC values despite the apparent presence of airway wall thickening, scarring, and airway remodeling.

Example—Computing Lung Cancer Risk Index

Figure 9:
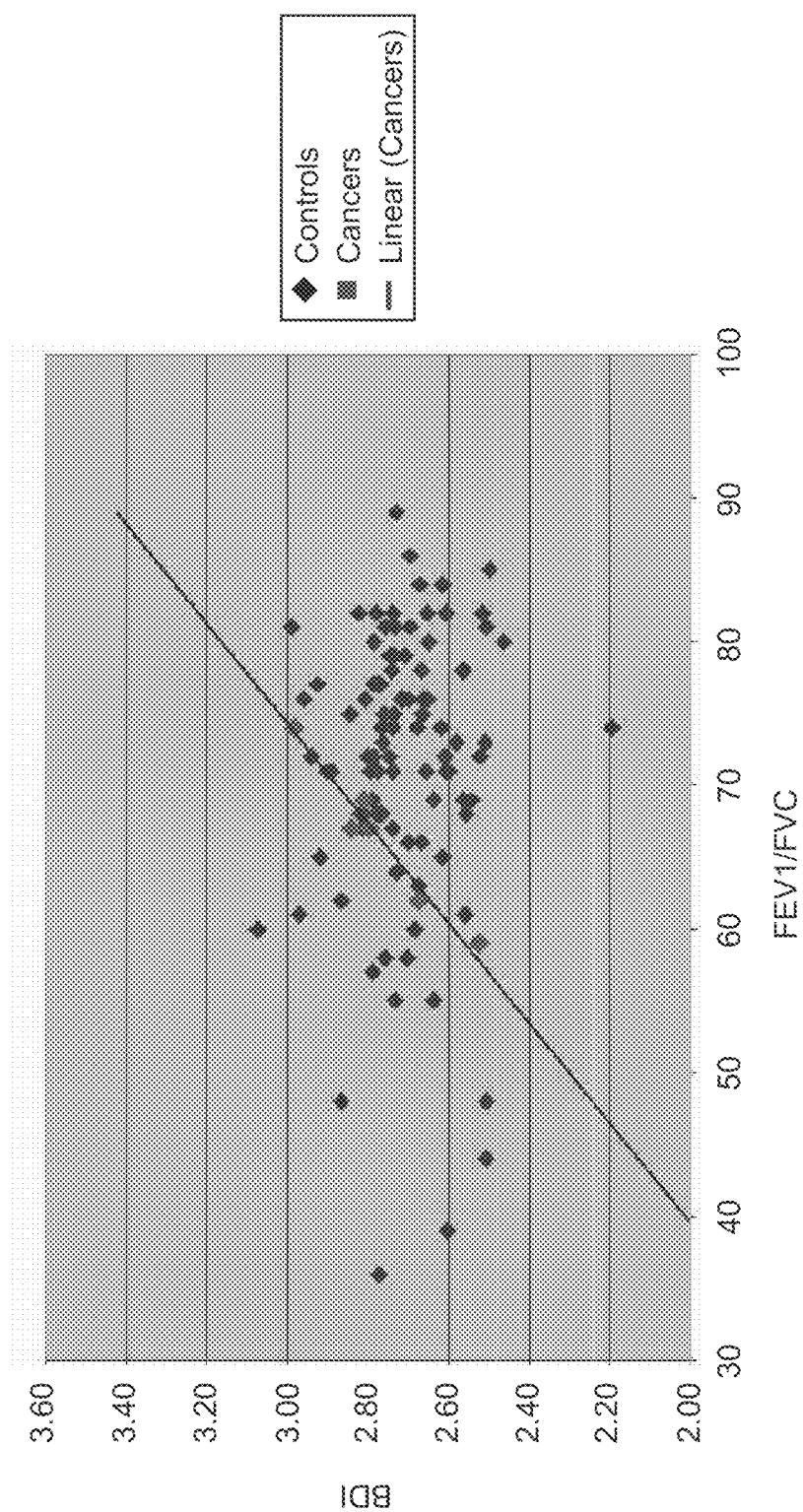
FIG. 9 is a scatter plot/graph showing BDI on the vertical axis plotted against FEV1/FVC plotted on the horizontal axis.

In this example, a plot of the BDI and FEV1/FVC values computed for cancer patients in the development dataset, described herein, revealed a near linear trend for the 6/13 patients that were scanned with 1 mm slice thickness and had FEV1/FVC values greater than 55%. This plot is shown in FIG. 9. A linear regression was computed for these cancer data points and distance to this line was used to compute the LCRI. It should be noted that four cancer cases had FEV1/FVC scores greater than 55%, but were scanned at 1.25 mm slice thickness. Consistent with the 1 mm slice thickness cancer data linear regression, the 1.25 mm slice thickness data points had a similar slope but had lower BDI values. This was likely due to an inability of the scanner correction method to fully account for partial volume artifact.

Example—Age and Pack Year Distribution

Figure 10:
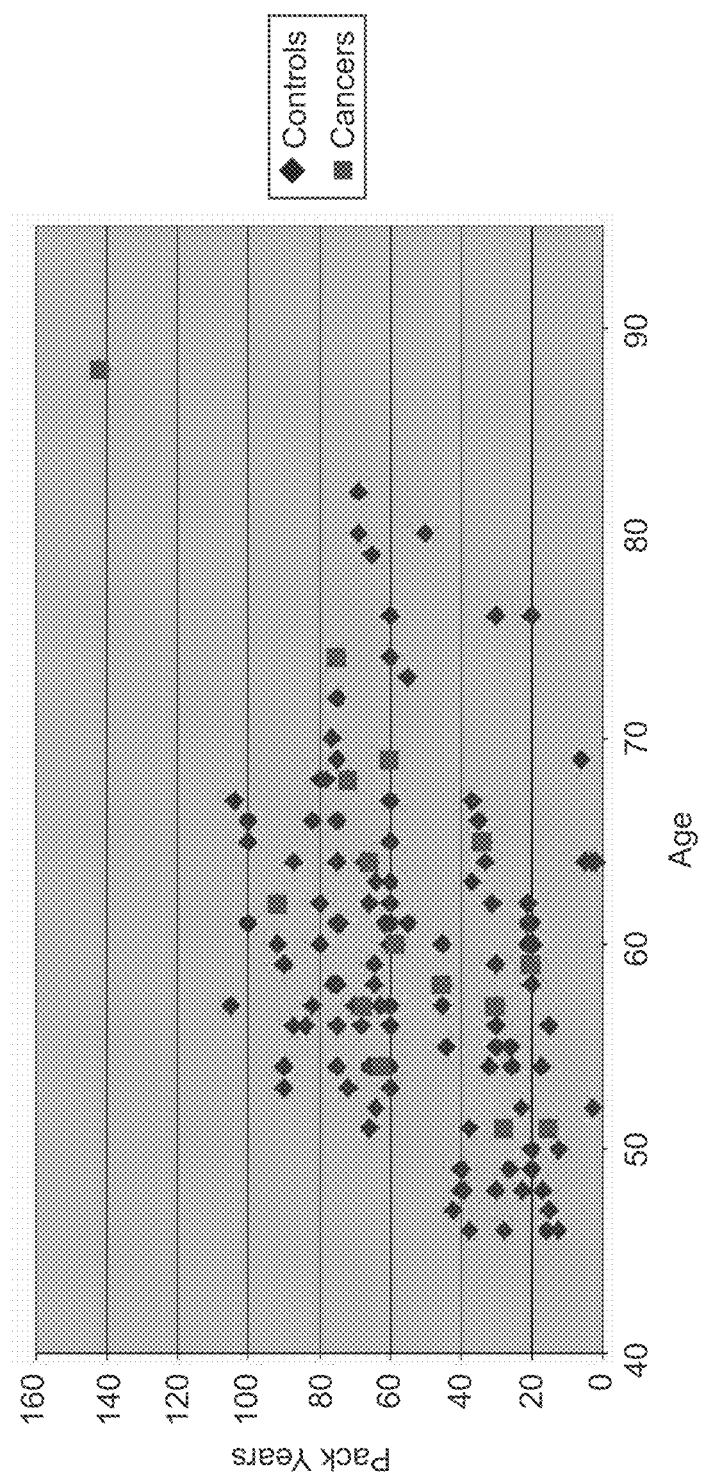
FIG. 10 is a scatter plot/graph showing pack years on the vertical axis plotted against age on the horizontal axis.

Referring to FIG. 10, HRCT data and FEV1/FVC data were obtained and the manual measurement technique was applied. Here, the BD and CD measurements were largely obtained in one reading session and without knowledge of the cancer status or FEV1/FVC values of the individual.

Example—BDI and FEV1/FVC Values

Figure 11:
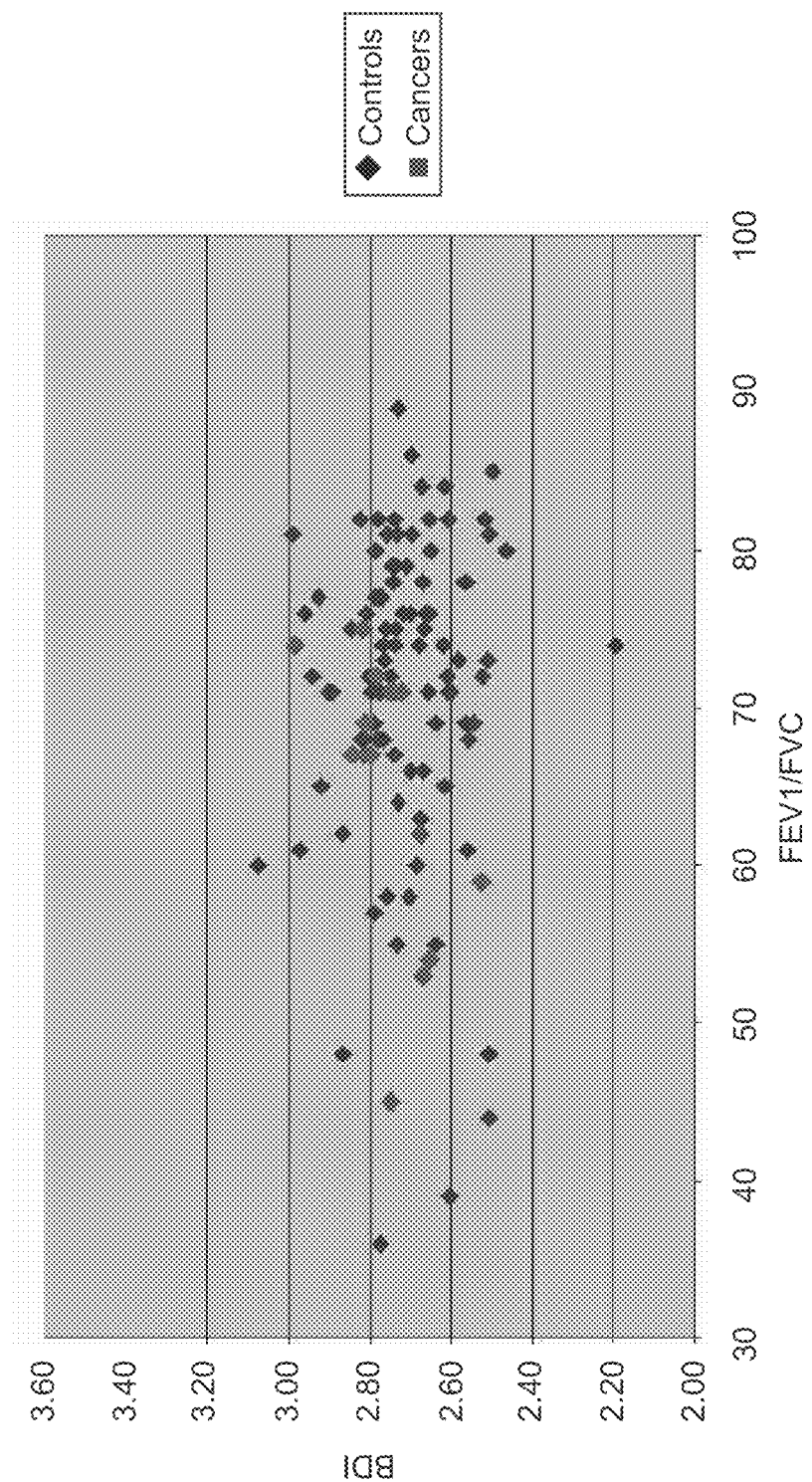
FIG. 11 is a scatter plot/graph showing BDI on the vertical axis plotted against FEV1/FVC plotted on the horizontal axis, but does not show the regression line.

Referring now to FIG. 11, HRCT scans of early lung cancer cases were reviewed along with four to five age, gender, and pack year matched control cases for each cancer case plus some additional HRCT cases. All subjects were scanned as part of an early lung cancer screening study. Most of the cases were male. Due to a lack of a clear gender distinction in the early results, gender was not used in the LCRI method or the reporting of results. Datasets with a slice thickness greater than 1.25 mm or those that contained excessive image noise or motion were not measured. All cases were scanned at low dose on the Siemens scanners shown in Table 1 (except for 1 Somatom Plus4 scan not measured due to poor coverage). A B60f reconstruction kernel was used, except for a few B80f cases. A total of 15 cancer cases and 122 control cases were provided for analysis, but 22 were not analyzed due to insufficient slice thickness or poor image quality. Of these 22, two cancer cases were excluded, one due to a 3 mm slice thickness and the other due to limited coverage of the lung. The age and pack years distribution for this data collection is shown in FIG. 10.

FIG. 11 shows a plot of BDI and FEV1/FVC scores for all cancers and controls that were measured. There is a trend in this measurement space that places healthy uninjured lungs in the bottom right corner and highly damaged lungs toward the top left corner

Example—LCRI Versus Age

Figure 12:
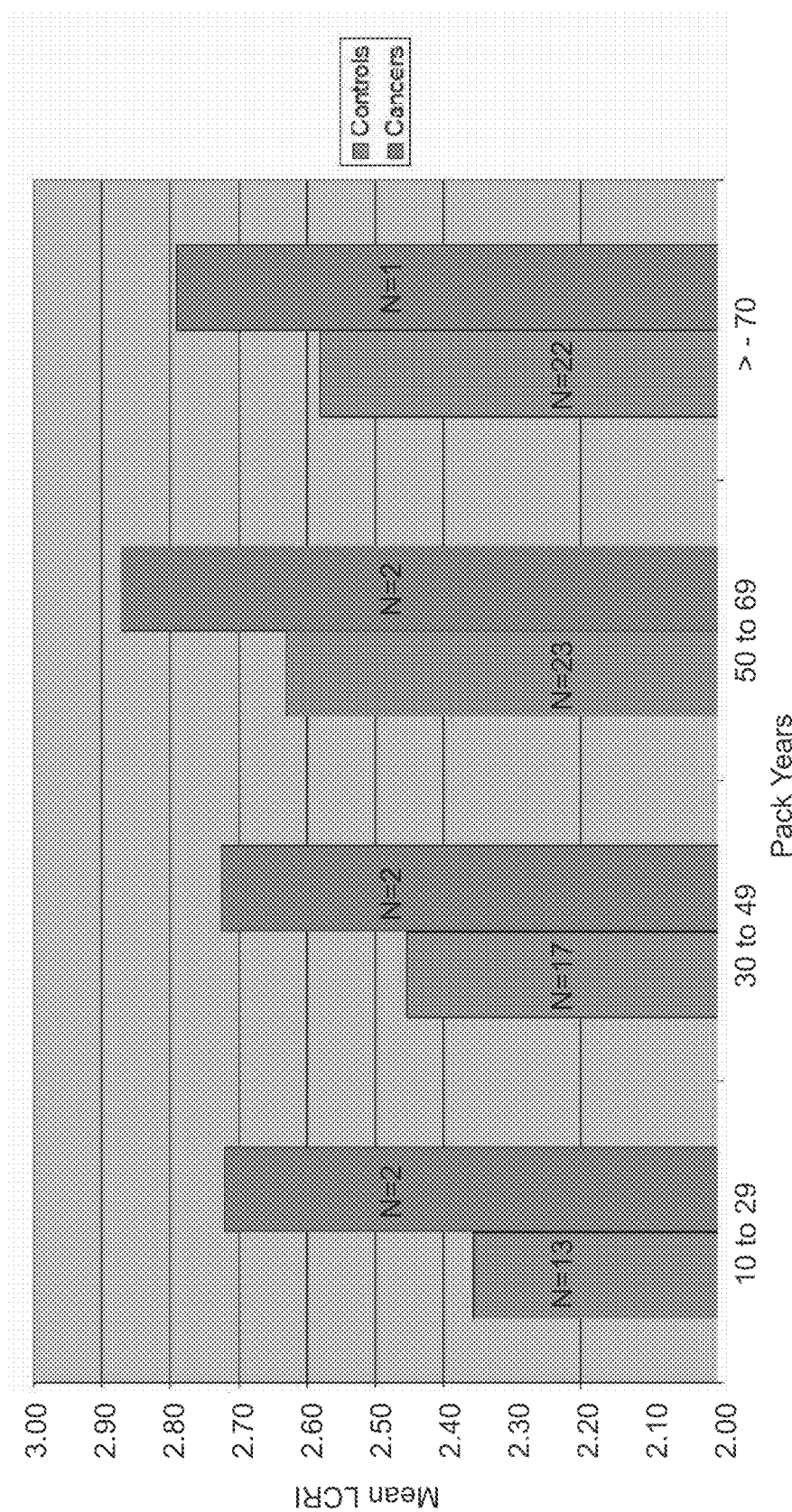
FIG. 12 is a bar graph showing mean LCRI values on the vertical axis against ranges of ages within age-related groups of pack year data.
Figure 13:
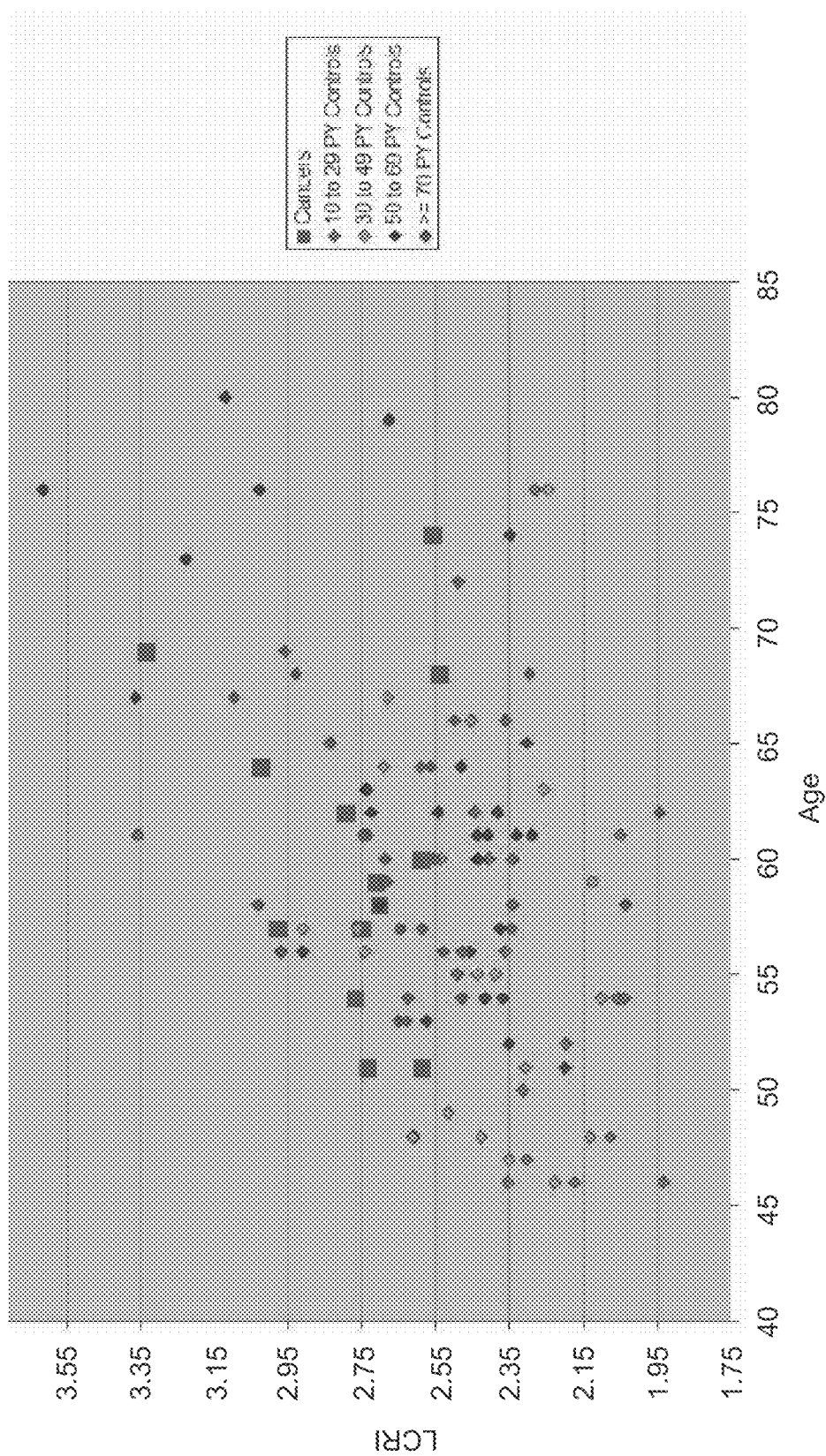
FIG. 13 is a scatter plot/graph of LCRI on the vertical axis plotted against Age on the horizontal axis.

Referring now to FIGS. 12 and 13, FIG. 12 shows the mean LCRI values for subjects with varying pack years. Only cases scanned with 1.0 mm slice thickness were used for this analysis in order to avoid variability associated with partial volume artifact. The control cases appear to show increasing LCRI values. All seven cancer cases had an LCRI value of 2.70 or greater. Finally, a plot of LCRI versus age for all cases is shown in FIG. 13. Pack year groups are shown in different colors and appear to demonstrate a progression of risk with increasing age and smoking exposure.

Example—An Automated Method

In this example, there is provided an automated method for estimating an individual's risk of developing lung cancer. Using the Lung Cancer Risk Index (LCRI) which consists of a combined measurement of maximal bifurcation calcification in HRCT and a corresponding FEV1/FVC score, we replace the manual method of measuring bifurcation calcification with a more robust and automated solution. This fully automated method allows for much faster experimentation and refinement of the method and also removes the inter- and intra-reader variability of a manual method. An automated method for computing the LCRI involves 4 main steps. First, the full 3D airway tree down to 5 branching levels is fully segmented from the CT scan. Second, the location of each bifurcation and the 3D extent of its carnal ridge is robustly identified. Third, an analysis of the maximal calcification in the vicinity of the carnal ridge as well as an estimate of the average calcification burden around the bifurcation is measured. An estimate of the full distribution of bifurcation calcification burden in the airways is established when all bifurcations have been processed and a Bifurcation Damage Index (BDI) for the patient is then computed. Fourth, the patient's FEV1/FVC score and BDI are combined using a linear classifier to form an overall Lung Cancer Risk Index (LCRI).

Example—Airway Segmentation Software

Figure 14:
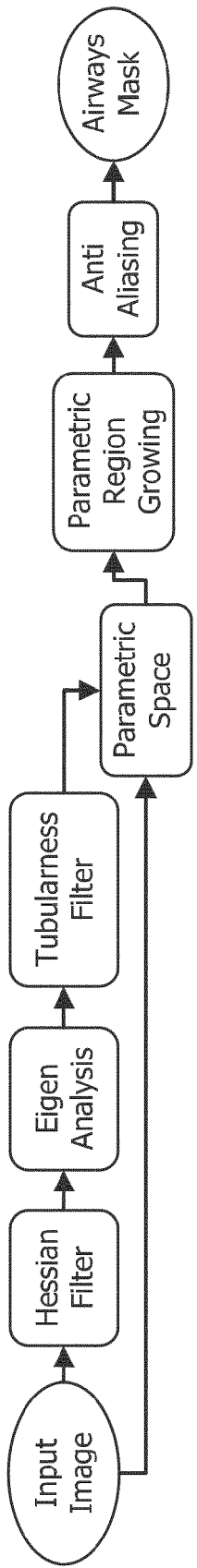
FIG. 14 is a box and arrow chart showing the pipeline for airway segmentation.

Referring now to FIG. 14, in this example, a software module to automatically detect and track the airway tree in low dose HRCT scans is provided. Highly accurate airway segmentation is important since failures in segmentation will degrade the estimation of the distribution of bifurcation calcification. The resulting segmentation is then utilized to identify bifurcations and serve as scaffolding for defining the regions of pixels that are used for estimating the LCRI.

Airway segmentation is based on the two main characteristics of airways: tubular shape and HU intensity values similar to air. The tubular shape is measured with the method proposed by Sato et al, [1998, Medical Image Analysis 2:143-168] based on the Eigen analysis of the image Hessian matrix computed at multiple scales. The scales which are considered are those in the range of diameters expected for the airways between the first and fifth branching levels. For every pixel this method computes a tubularness value. For every given pixel in the image, the values of HU intensity and tubularness are used as positions in a 2D parametric space. The airways structure are extracted by using a region growing method combining spatial connectivity in the 3D CT scan with a similarity criterion based on proximity in the 2D parametric space of HU intensity and tubularness. The seed points for the region growth are selected automatically based on the large expected radius of the Trachea, which provide a very unique signature in the CT dataset.

Figure 15:
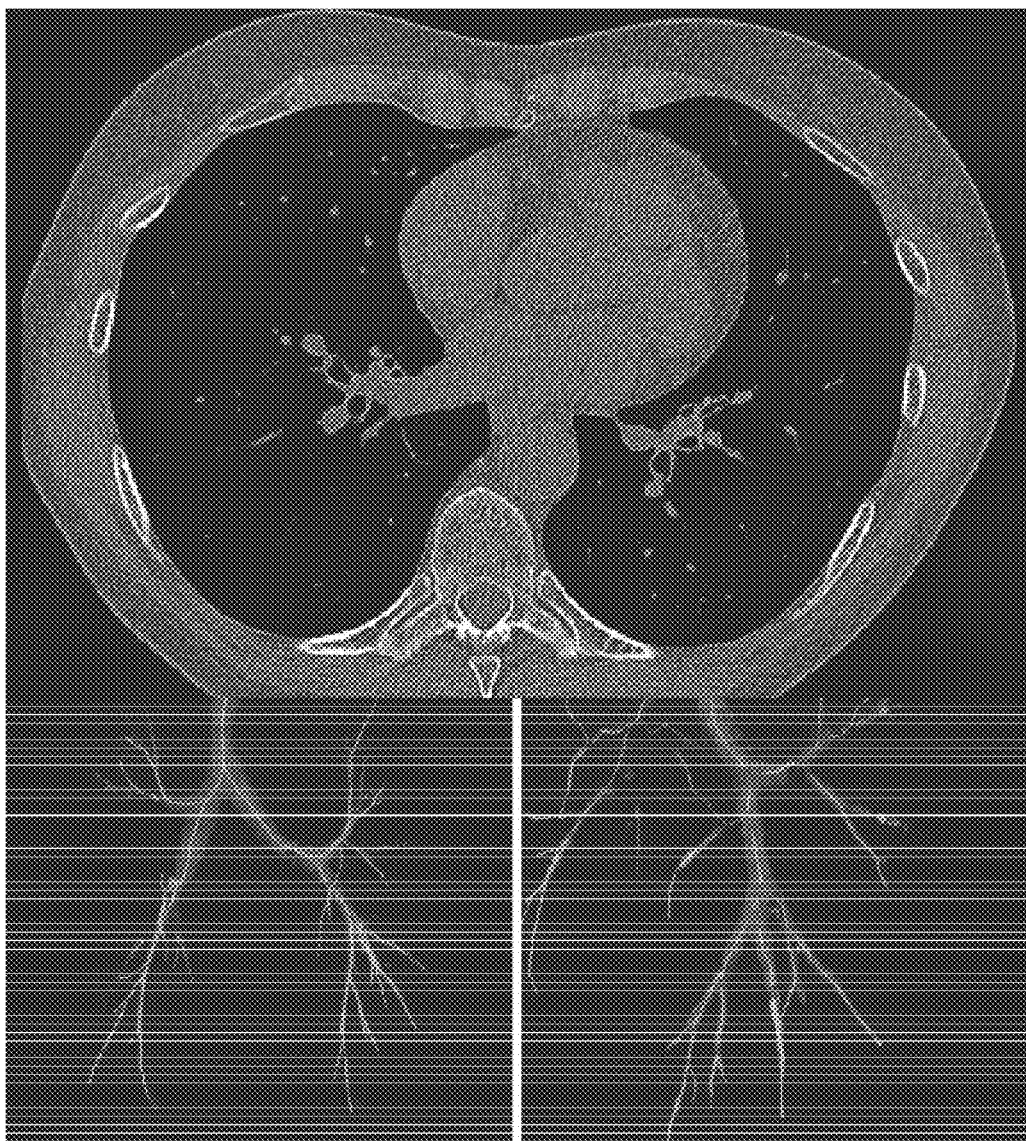
FIG. 15 (top) is a CT image "slice" showing contours from airway segmentation; (bottom left) shows medial airway surface line extracted using the LA04 method; (bottom right) shows how bifurcations on the medial line are automatically extracted and parent/child relationships are computed.

The output of the parametric region growing filter is a binary image, which unfortunately produces staircase effects when iso-surface extraction is performed. These staircases generate artifacts in the subsequence bifurcation analysis and therefore, to prevent them, an Anti-Alias level-set-based filter is added at the end of this pipeline to smooth the image before the final surface extraction. The Anti-Alias filter guarantees that the surface will not be displaced by more than one voxel [29]. FIG. 14 illustrates the image processing pipeline consisting mostly of filters that are currently available in the ITK toolkit. Segmentation results are shown in FIG. 15. It is contemplated that when dataset anomalies are found, they will be analyzed and algorithm corrections will be developed. Cycles of algorithm evaluation and algorithm correction may then be performed iteratively until all major segmentation issues are resolved.

Example—The Pipeline for Airway Bifurcations and Carinal Ridge

Figure 16:
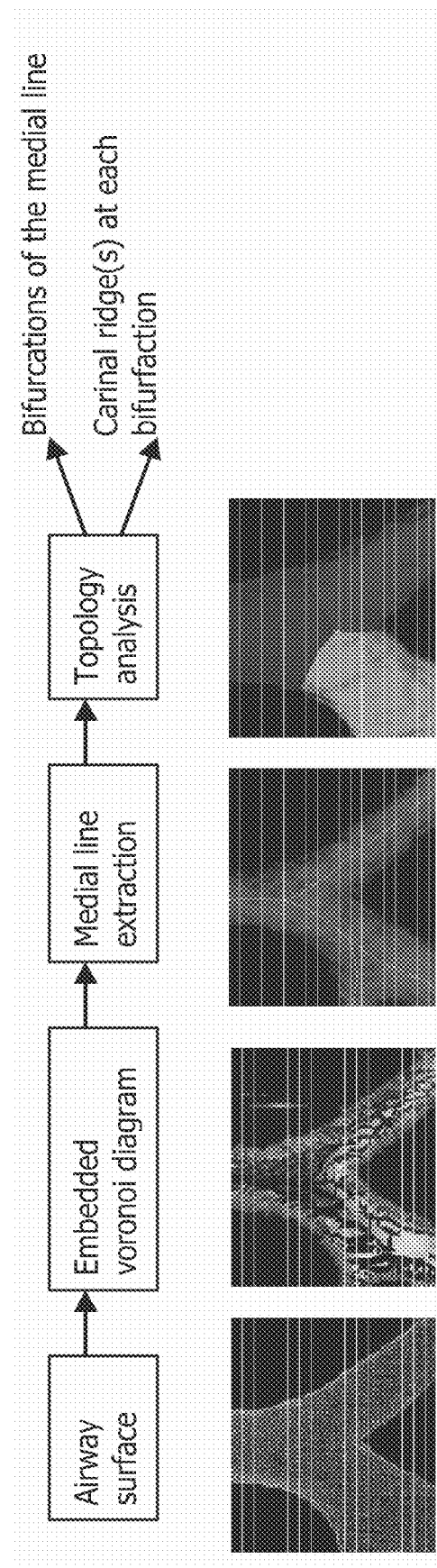
FIG. 16 is a combination of box and arrow diagram placed above four images, (i) the airway surface, (ii) embedded voronoi diagram, (iii) medial extraction line, and (iv) topology analysis. These are used to identify bifurcations of the medial line and carinal ridges at each bifurcation.

Referring now to FIG. 16, there is provided a pipeline that is used to identify the airway bifurcations and carinal ridge. A module is then developed that automatically identifies each bifurcating and carinal ridge down to 5 branching levels. Human airways, and particularly those of aging smokers, exhibit a large degree of variation in airway geometry including a very wide range of airway branching angles, changes in airway diameter, curvature along airway segments and at bifurcations, and as many as 4 branches occurring simultaneously. In addition, the presence of ridges, sputum, and locations of partial airway narrowing adds further complexity to this task.

This method is based on prior work on the analysis of geometry of bifurcating vascular trees [Antiga et al., 2004 IEEE Trans. Medical Imaging 23:704-713]. Here, there is shown a surface enclosing the segmentation of the airway, up to the 5th level. The surface is capped if necessary to ensure that it is closed. The medial line of this surface is extracted as outlined in Antiga et al. This involves computing the embedded voronoi diagram of the points in the airway surface, from their Delaunay tesselation. The embedded voronoi diagram is the a subset of the voronoi diagram, internal to the object and is obtained by removing from the Delaunay tessellation, the tetrahedra whose circumcenter falls outside the airway surface. The medial line is guaranteed to lie on the boundaries of the voronoi polygons. The next step is to solve the Eikonel equation on this voronoi diagram, with a speed function inversely proportional to the radius of the voronoi spheres using the fast marching method. This method produces an accurate depiction of the medial line, its accuracy determined by the mesh resolution, which is denser than the image resolution. The radius at each point along with the medial line is given by the radius of the voronoi spheres. The topology of the resulting medial-line tree is analyzed to detect splits and the parent, children at each bifurcation. FIG. 16 illustrates this image processing pipeline. All of these methods are currently available in ITK [www.itk.org], VTK [www.vtk.org] and VMTK [www.vmtk.org], under a BSD license.

To evaluate the dataset, tree like geometries are constructed analytically, whose carinal ridges can be analytically computed and which use these to validate the carinal ridge extraction algorithm. Evaluation on the development datasets may also be done visually by checking if the medial line is extracted correctly, and that the carinal ridge(s) at each bifurcation are computed.

Example—Bifurcation Calcification Analysis

As described herein, calculation of the Bifurcation Damage Index (BDI) requires accurate measurement of (i) a Bifurcation Density (BD); (ii) a Comparison Density (CD); and (iii) a scanner Correction Factor (CF). In this example, there is provided an automated method used to calculate the BDI. With a fully automated algorithm, measurement of all upper airway bifurcations in a case is possible and which fit a distribution function to estimate the full distribution of damage. Where this data is represented by a standard statistical distribution, an analysis of the upper tail of this distribution may create a BDI for the entire lung region in the patient. This distribution may be expected to be more resilient to a few outlier bifurcation values.

Example—Comparison Density

Figure 17:
FIG. 17 is an enhanced image showing the location of the carinal ridge (red) and the CD calculation (blue plane).

Referring now to FIG. 17, in this example, there is provided another improvement of the Bifurcation Damage Index, namely with the calculation of CD. First, a solution is implemented performs similar operations as the manual measurement. Then, measurements are taken of increasing amounts of cartilage surrounding the bifurcation and spatially interpolating these values to determine the CD value at the location of BD. This prevents a single cartilage ring with unrelated density values from dominating the CD calculation and therefore results in a more robust BDI measurement.

In practice, CD is obtained since a segmentation of the airway down to the 5th generation as well as the segmentation of the carinal ridge near each bifurcation has already been found. The Insight ToolKit (ITK) [31] has iterators which allow neighborhoods of an image to be walked and manual operations to be applied at each of the voxels within the neighborhood. The carinal ridge segmentation is used as the neighborhood to be walked, and calculated from each voxel of the image in the neighborhood is the maximum 26-connected pair to arrive at the BD value for the bifurcation. To get CD, the airway is walked up a distance c from the bifurcation using a previously calculated center line. A perpendicular plane will be used to cut the image perpendicular to the airway tree at this location and a distance map will be generated that gives the radial distance r from the airway boundary.

The algorithm may be evaluated in two parts. First, a set of digital phantoms is developed with known BDI and predetermined airway and bifurcation segmentations are used to validate the mathematics of the system. Second, given the development data set and the segmentations of the airway tree and bifurcations from the previous sections, a number of the bifurcation BDI values are hand-calculated and compared to the values computed by the program.

Example—Lung Cancer Risk Estimation

In this example, there is disclosed a method and system for estimating the overall LCRI by analysis of FEV1/FVC and BDI values for various groups in the development dataset and by establishing the geometry and direction needed to create an increasing risk index. Linear regression strategy is used to determine the direction of increasing lung cancer risk, but more advanced classification methods such as linear discriminant analysis and support vector machine analysis, are also contemplated as within the present inventive subject matter. These methods may include the data collected from the automated algorithm and/or available clinical information such as individual FEV1 and FVC values as well as pulmonary function test prediction percentages and clinical data such as age, pack years, and presence of emphysema.

Example—Evaluating the Automated Lung Cancer Risk Method

In this example, there is provided a method for evaluating the automated lung cancer risk method. Two metrics may be used to measure the performance of the automated LCRI method versus manual measurement. The first metric is the ability of the method to separate cancer cases from age and pack year matched controls. In addition, a good estimate of risk for developing lung cancer should correlate with increasing tobacco exposure. Thus the second metric is the degree of correlation between the calculated LCRI and self-reported pack years. A receiver operator characteristic (ROC) approach, including the calculation of the area under the curve (AUC) will be employed to fully understand the performance of the automated LCRI method versus the manual measurement method on the development dataset. A leave-one-out cross-validation approach may also be employed to better understand the confidence interval associated with the ROC curves.

Example BDI vs. FEV1/FVC Graph

Figure 18:
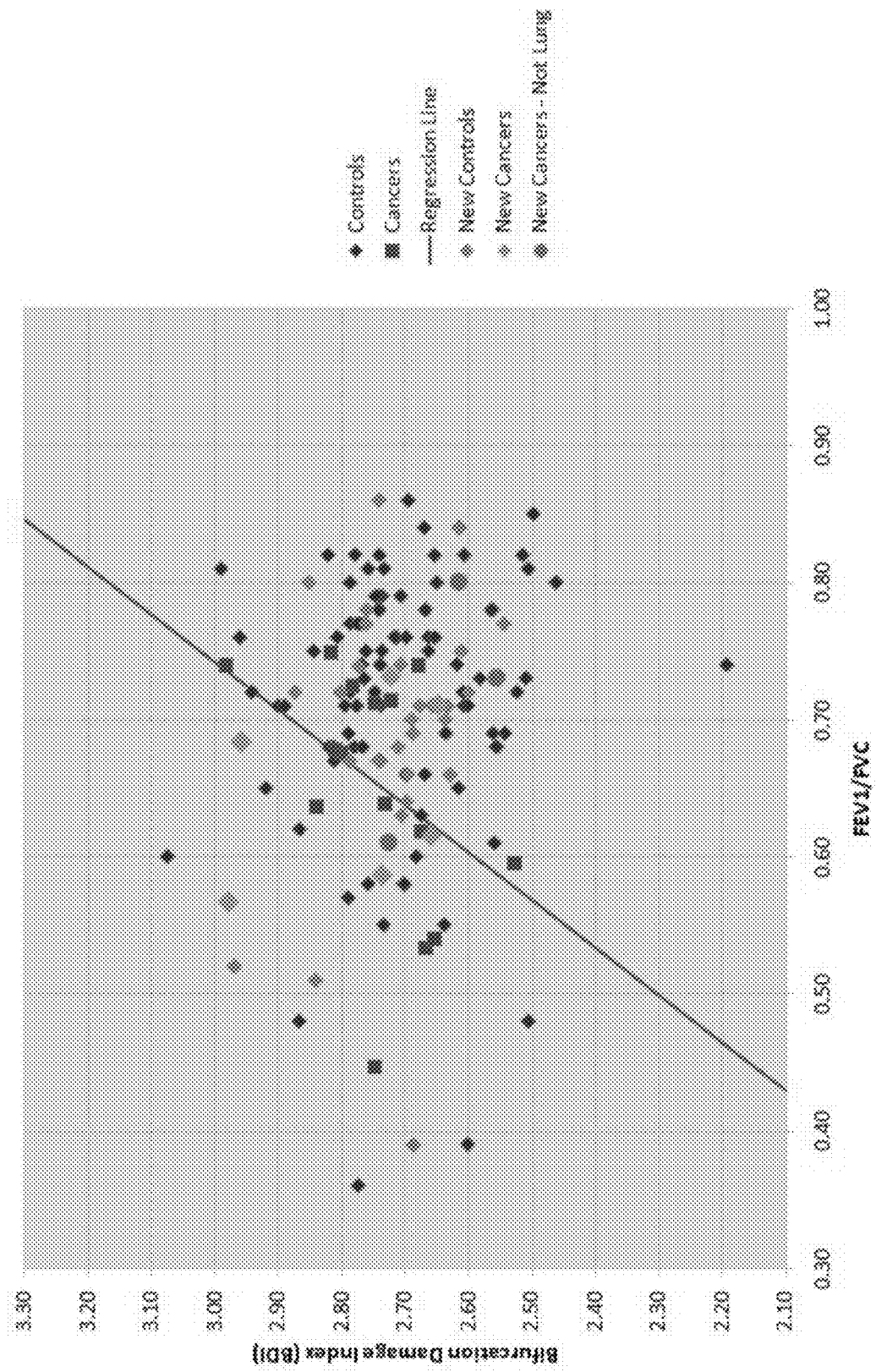
FIG. 18 is a graph of data points reflecting measurement scores and outcomes of lung cancer patients. The x-axis shows the Bifurcation Damage Index (BDI) and the y-axis shows the FEV1/FVC ratio measurements.

Referring now to FIG. 18, FIG. 18 is a graph of data points reflecting measurement scores and outcomes of lung cancer patients. The x-axis shows the Bifurcation Damage Index (BDI) and the y-axis shows the FEV1/FVC ratio measurements. FIG. 18 shows that there is a risk area where increased damage/calcification meets with decreased lung function/obstruction and the result is a much higher risk of lung cancer. Note that as patient measurements scores move down the FEV1/FVC scale from right to left, the risk of cancer increases. Note also that as damage increases, even in those with higher lung functions, the risk of lung cancer increases.

Finally, the regression line shows that when conditions are found indicating that a patient's damage and function measurements are moving from right to left across or toward the regression line, a patient risk of cancer increases.

References

[1] Henschke C I, Yankelevitz D F, Smith J P, et al. "CT screening for lung cancer: assessing a regimen's diagnostic performance." Clin Imaging 2004; 28:317-21.

[2] Imre Balásházy, Werner Hofmann and Thomas Heistracher, "Local particle deposition patterns may play a key role in the development of lung cancer," J Appl Physiol 94: 1719-1725, 2003.

[3] Official Statement of the American Thoracic Society, "Diagnosis and Initial Management of Nonmalignant Diseases Related to Asbestos," Am J Respir Crit Care Med Vol 170. pp 691-715, 2004.

[Chan2002] Edward D. Chan, Donald V. Morales, Carolyn H. Welsh, Michael T. McDermott, and Marvin I. Schwarz, Calcium Deposition with or without Bone Formation in the Lung, Am J Respir Crit Care Med Vol 165. pp 1654-1669, 2002.

[Chan2009] Hiang Ping Chan, Vanessa Tran, Craig Lewis, and Paul S. Thomas, Elevated Levels of Oxidative Stress Markers in Exhaled Breath Condensate, J Thorac Oncol. 2009; 4: 172-178.

[Vaughan2003] J. Vaughan, L. Ngamtrakulpanit, T. N. Pajewski, R. Turner, T-A. Nguyen, A. Smith, P. Urban, S. Hom, B. Gaston, J. Hunt, Exhaled breath condensate pH is a robust and reproducible assay of airway acidity. Eur Respir J 2003; 22: 889-894.

[Borrill2008] Zoe L Borrill, Kay Roy, Rupert S Vessey, Ashley A Woodcock, Dave Singh, Non-invasive biomarkers and pulmonary function in smokers, International Journal of COPD 2008:3(1) 171-183.

[Boulet2006] Louis-Philippe Boulet, Catherine Lemie're, Francine Archambault, Guy Carrier, Marie Claire Descary, and Francine Deschesnes. Clinical and Radiologic Features, Lung Function, and Airway Inflammation, Chest 2006; 129; 661-668.

[Kostikas2002] Konstantinos Kostikas, Georgios Papatheodorou, Konstantinos Ganas, Konstantinos Psathakis, Panos Panagou, and Stelios Loukides, pH in Expired Breath Condensate of Patients with Inflammatory Airway Diseases, Am J Respir Crit Care Med Vol 165. pp 1364-1370, 2002.

[Koczulla2009] Rembert Koczulla, Silvano Dragonieri, Robert Schot, Robert Bals, Stefanie A. Gauw, Claus Vogelmeier, Klaus F. Rabe, Peter J. Sterk, Pieter S. Hiemstra, Comparison of exhaled breath condensate pH using two commercially available devices in healthy controls, asthma and COPD patients. Respiratory Research 2009, 10:78.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

I claim:

1. A method of using a computer processor to assess an individual against lung disease risk comprising: receiving data representing lung X-ray images of an individual, using said data to calculate an X-ray attenuation score from one or more measurements of a density deviation at one or more airway bifurcation locations compared to a density value at a region surrounding the bifurcation, combining the X-ray attenuation score with a lung function score of the individual calculated from one or more lung function measurement tests selected from the group consisting of a CT lung function analysis, a spirometry test, a lung ventilation scan, a lung perfusion scan, and a pH value from an exhaled breath condensate test, and assessing of the individual against a lung disease risk index based on said combined X-ray attenuation score and lung function score.

2. The method of claim 1, further comprising wherein the spirometry test is FEV1/FVC.

3. The method of claim 1, further comprising wherein the CT lung function analysis includes a CT wall thickness measurement, emphysema measurement, or both.

4. The method of claim 1, further comprising wherein the X-ray attenuation score is obtained from an imaging modality selected from the group consisting of a CT scan, chest X-ray, digital radiography, X-ray tomosynthesis, and computer aided X-ray radiography.

5. The method of claim 1, further comprising wherein the density deviation is a measure of calcification, particle deposition, ossification, or combinations thereof.

6. The method of claim 1, further comprising the steps of measuring over time the lung disease risk index and establishing a disease trajectory for the individual.

7. The method of claim 5, further comprising the steps of measuring over time the lung disease risk index and establishing a trajectory for the individual.

8. The method of claim 5, wherein the CT lung function scan includes measurements of a shape change in the one or more bifurcations comprising a thickening of the lung tissue at the bifurcation or surrounding tissue, or a loss of tissue or hole in the lung tissue at the bifurcation or surrounding tissue.

9. The method of claim 1, further comprising wherein measuring density deviations further comprises measuring the sum of the logs of maximum HU density deviations from nearby low exposure regions along the airway tree in a CT scan.

10. The method of claim 1, further comprising wherein the lung disease risk index is a lung cancer risk index.

11. The method of claim 1, further comprising the step of identifying locations that represent high lung cancer risk.

12. The method of claim 1, further comprising the step of identifying specific lung regions or lobes that represent high lung cancer risk by calculating a region-specific or lobe-specific lung cancer risk index by combining a region-specific X-ray attenuation score with a region-specific lung function score, wherein the region-specific X-ray attenuation score is obtained by applying a lung region-specific classifier to the X-ray attenuation score to identify lung region-specific data subsets of bifurcation locations, and the region-specific lung function score is obtained by modifying the lung function score based upon factors affecting regional airflow.

13. An imaging system for lung disease, comprising: an X-ray imaging modality; and a computer programmed to: receive data representing lung X-ray images of an individual, use said data to calculate an X-ray attenuation score from one or more measurements of a density deviation at one or more airway bifurcation locations compared to a density value at a region surrounding the bifurcation, and combine the X-ray attenuation score with a lung function score of the individual calculated from one or more lung function measurement tests selected from the group consisting of a CT lung function analysis, a spirometry test, a lung ventilation scan, a lung perfusion scan, and a pH value from an exhaled breath condensate test, wherein said combined X-ray attenuation score and lung function score provides an assessment of the individual against a lung disease risk index.

14. A method for preparing a data set that provides an estimation of a patient's lung cancer risk, using the imaging system of claim 13, comprising:
   (i) obtaining a measurement of the pH of the lung using an exhaled breath condensate (EBC) device;
   (ii) obtaining results of a pulmonary function test obtained by spirometry;
   (iii) obtaining a measurement of the level of X-ray attenuation in the airways and calculating a bifurcation damage index (BDI); and,
   (iv) combining the pH, spirometry, and X-ray attenuation into a single lung cancer risk index.

15. The method of claim 14, further comprising the step of applying a classifier to the distribution of measurements to separate lung cancer risk levels and patient sub-populations, COPD patient populations, individuals at risk and patients having other pulmonary related diseases.

16. The imaging system of claim 13, further comprising wherein the imaging modality is selected from the group consisting of a CT scan, chest X-ray, digital radiography, X-ray tomosynthesis, and computer aided X-ray radiography.

17. The imaging system of claim 13, further comprising wherein the density deviation is a measurement of calcification, particle deposition, ossification, or combinations thereof.

18. The system of claim 13, further comprising wherein the imaging modality is a multiple energy CT scan and provides features to further distinguish individual response to exposure.

19. The system of claim 13, further comprising wherein the computer is programmed to compare changes between one or more assessments of lung cancer risk index.

20. The system of claim 13, further comprising wherein combining measurements into a lung cancer risk index further comprises adjusting the metric for additional clinical data such as age, gender, smoking history, comorbidity, and family history.

21. A non-transitory computer readable medium, comprising software code portions for implementing the steps of the method as set forth in claim 1, when said medium is run on a digital computer.

* * * * *